(12) United States Patent
Gagliardi et al.

(10) Patent No.: US 8,729,098 B2
(45) Date of Patent: May 20, 2014

(54) TERTIARY 8-HYDROXYQUINOLINE-7-CARBOXAMIDE DERIVATIVES AND USES THEREOF

(75) Inventors: Stefania Gagliardi, Vimercate (IT);
Simone Del Sordo, Treviglio (IT);
Federico Mailland, Lugano (CH);
Michela Legora, Appiano Gentile (IT)

(73) Assignee: Polichem SA, Luxembourg (LU)

( * ) Notice: Subject to any disclaimer, the term of this patent is extended or adjusted under 35 U.S.C. 154(b) by 32 days.

(21) Appl. No.: 13/519,206

(22) PCT Filed: Dec. 28, 2010

(86) PCT No.: PCT/EP2010/070790
§ 371 (c)(1),
(2), (4) Date: Aug. 15, 2012

(87) PCT Pub. No.: WO2011/080264
PCT Pub. Date: Jul. 7, 2011

(65) Prior Publication Data
US 2012/0309751 A1    Dec. 6, 2012

(30) Foreign Application Priority Data

Dec. 29, 2009  (EP) .................................... 09180902

(51) Int. Cl.
*A61K 31/04* (2006.01)
*C07D 215/38* (2006.01)

(52) U.S. Cl.
USPC .......................................... 514/314; 546/168

(58) Field of Classification Search
USPC .......................................... 546/168; 514/314
See application file for complete search history.

(56) References Cited

U.S. PATENT DOCUMENTS

| 6,194,413 B1 | 2/2001 | Bhatnagar et al. |
| 6,525,042 B1 | 2/2003 | Kobayashi et al. |

FOREIGN PATENT DOCUMENTS

| EP | 1669348 | 6/2006 |
| JP | 2001/294572 | * 10/2011 |
| WO | WO98/11073 | 3/1998 |

OTHER PUBLICATIONS

Godard, CA109:73299, abstract only of J Org Chem, vol. 336(1-2), pp. 1-12, 1987.*
Baret, P. et al, Journal of the American Chemical Society, vol. 117, No. 38, p. 9760-9761, 1996.
Godard, et al., Journal of Organometallic Chemistry, vol. 336, p. 1-12, Jan. 1, 1987.
International Search Report With Written Opinion for PCT/EP2010/070790 of Feb. 10, 2011.
IPRP for PCT/EP2010/070790 of Mar. 8, 2012.
Bastert J. et al, Int. J. Antimicrob. Agents, 2001; 17, 81-91.
Cornely O. A. et al, Clin. Infect. Dis., 2007; 44, 1289-1297.
Dictar M. O. et al, Med Mycol., 38 Suppl. 1, 251-258.
Dumaine R., Roy M. L., Brown A. M., J. Pharmacol. Exp. Ther., 1998; 286, 727-735.
Hamacher J. et al, Eur. Respir. J., 1999; 180-186.
Johnson L. B., Kauffman C. A., Clin. Infect. Dis., 2003, 36, 630-637.
Khan S. A., Wingard J. R., Natl. Cancer Inst. Monogr. 2001; 29, 31-36.
Korting H. C. et al, Anitmicrob. Agents Chemother., 1993; 37, 2064-2068.
Magro C. M. et al, J. Cutan. Pathol., 2008; 35, 74-81.
Perveze Z. et al, Liver Transpl., 2007; 13, 162-164.
Sarosi S. A., Davies S. F., West J. Med., 1996; 164, 335-340.
Schelenz S., J. Antimicrob. Chemother. 2008; 61, Suppl 1, 31-34.
Sidoroff A. et al, Br. J. Dermatol., 2007; 15, 989-996.
Trof R. J. et al, Intensive Care Med., 2007; 33, 1694-1703.
Cho-Schultz et al., J. Comb. Chem., 2009, 11, 860-874.

* cited by examiner

*Primary Examiner* — D M Seaman
(74) *Attorney, Agent, or Firm* — Hueschen and Sage

(57) ABSTRACT

New tertiary 8-hydroxyquinoline-7-carboxamide derivatives of general formula (I) and pharmaceutically acceptable salts thereof are disclosed.

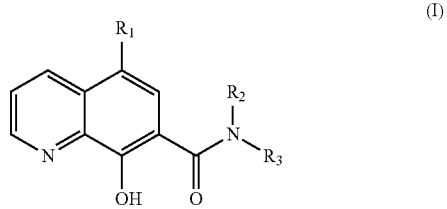

These compounds are useful as antifungal agents. Specifically, these compounds were tested against *Tricophyton Rubrum*, *Tricophyton Mentagrophytes*, *Aspergillus Niger* and *Scopulariopsis Brevicaulis*. These compounds are also active against *Candida* species such as *Candida Albicans* and *Candida Glabrata*.

13 Claims, No Drawings

TERTIARY 8-HYDROXYQUINOLINE-7-CARBOXAMIDE DERIVATIVES AND USES THEREOF

The present invention provides new tertiary 8-hydroxyquinoline-7-carboxamide derivatives and pharmaceutically acceptable salts thereof, which are useful as antifungal agents and a process for their preparation. Specifically, these compounds were tested against *Tricophyton Rubrum, Tricophyton Mentagrophytes, Aspergillus Niger* and *Scopulariopsis Brevicaulis*. Many of these compounds are also active against *Candida* species such as *Candida Albicans* and *Candida Glabrata*.

BACKGROUND OF THE INVENTION

Pathogenic fungi can be divided in two categories: fungi that are able to induce diseases in normal subjects and less invasive fungi that are able to produce diseases only in critically ill hosts. In the past two decades there was a significant increase in the incidence of invasive opportunistic fungal infections and associated morbidity and mortality. This is mainly due to the major advances in modern medicine that have increased the survival of critical patients such as those in intensive care units (ICU) with intravascular and urinary catheters, total parenteral nutrition and hemodialysis or connected to ventilatory systems.

*Candida* species commonly cause nosocomial blood stream infections among patients in the ICU. The UK hospitalized incidence of candidemia is about 3 per 100,000 bed days, and 40% to 52% of all cases occur in ICU (Schelenz S., *J. Antimicrob. Chemother.* 2008; 61, Suppl 1, 31-34). This kind of mycoses is frequently associated with considerable morbidity and mortality. The attributable mortality rate is about 38%, although it can vary between 5% and 71%. During recent years there was a rising incidence of invasive pulmonary aspergillosis in patients admitted to ICU. The disease incidence ranges from 0.3% to 5.8% with an overall mortality rate exceeding 80% (Trof R. J. et al, *Intensive Care Med.*, 2007; 33, 1694-1703). Critically ill patients are at risk to develop disturbances in immunoregulation during their stay in the ICU, which render them more vulnerable to fungal infections. Risk factors such as chronic obstructive pulmonary disease, prolonged use of steroids, advanced liver disease, chronic renal replacement therapy, near-drowning and diabetes mellitus have been described.

There was a dramatic increase also in the number of immunocompromised patients especially in the fields of solid organ and bone marrow transplantation, autoimmune syndromes, acquired immune deficiency syndrome (AIDS) and oncology.

About 40% of bone marrow transplant population develops invasive fungal infection (Khan S. A., Wingard J. R., Natl. Cancer Inst. Monogr. 2001; 29, 31-36). *Candida* and *Aspergillus* species are the most common pathogens responsible for nosocomial superficial and invasive mycoses in hematologic malignancies and bone marrow transplanted patients. In these patients the mortality associated with the systemic candidosis is very high (50-90%). Regarding solid organs transplantation, infective complications are more frequent in lung-transplanted patients. In addition to the immunosuppressive regimen, the increased susceptibility is mainly due to the constant exposure to the external environment. Parallel to immunosuppressive treatment intensity, invasive fungal infection may occur during the first days after surgical operation, its frequency is highest in the first two months and decreases after 6 months but it can occur also years after transplantation (Hamacher J. et al, *Eur. Respir. J.*, 1999; 13, 180-186).

Invasive fungal infections are also frequent in other kind of solid organ transplantation such as kidney and liver transplants for which incidence of 5 to 50% are reported (Dictar M. O. et al, *Med Mycol.*, 2000; 38 Suppl. 1, 251-258).

Mycoses are one of the major causes of morbidity in patients with AIDS and the incidence and severity of these infections increase with disease progression and the consequent impairment of T-cell-mediated immunity. The incidence of the different mycoses is closely related to the endemic opportunistic fungi present in the area of residence. Generally speaking the most frequent mycoses that affect AIDS patients are histoplasmosis, blastomycosis, coccidioidomycosis and paracoccidiomycosis (Sarosi G. A., Davies S. F., West *J. Med.*, 1996; 164, 335-340).

Mucosal *Candida* infections are also extremely common. In normal patients all these mycosis are usually self-limited but in immunodepressed patients become highly invasive resulting in progressive and widespread dissemination.

Moreover, the increase of mycosis caused by organism resistant to current therapies became evident over recent years. This phenomenon is particularly evident for fungal infections caused by *Candida albicans* and fluconazole and other azoles (Bastert J. et al, *Int. J. Antimicrob. Agents*, 2001; 17, 81-91). The antimycotic drugs currently available are not fully satisfactory due to their limited activity spectrum and to the heavy side effects associated to their use. The polyene drug Amphotericin B, for example, is active against *Aspergillus*, Zygomycete and other molds anyway, and due to its toxicity the licensed dosage for treatment of invasive mycosis is 3-5 mg/kg per day. In highly immunocompromised patients with invasive aspergillosis, liposomal encapsulated Amphotericin B, daily administered at 3 mg/kg, gave a favorable response in 50% of patients and 12-week survival rate of 72% (Cornely O. A. et al, *Clin. Infect. Dis.*, 2007; 44, 1289-1297). The drug induced nephrotoxicity and hypokalemia in 14-16% of the patients. When daily administered at 10 mg/kg, Amphotericin B did not give any additional benefit and caused higher rates of nephrotoxicity (31%).

Azoles, introduced in the second half of the 1970s, are blockers of ergosterol synthesis. The use of the drugs belonging to this family is limited by their narrow spectrum of activity. Voriconazole, for example, is more active than Amphotericin B for the treatment of invasive aspergillosis but has no activity against zygomycetes (Johnson L. B., Kauffman C. A., *Clin. Infect. Dis.*, 2003, 36, 630-637). The azoles employment is also limited by the induction of several side effects. Azoles interact with mammalian p450 enzymes resulting in interference with the metabolism of other drugs and, in addition, some azoles such as ketoconazole are able to block the cardiac potassium channel Kv1.5 causing Q-T prolongation and 'torsade de pointes' (Dumaine R., Roy M. L., Brown A. M., *J. Pharmacol. Exp. Ther.*, 1998; 286, 727-735).

Allylamines such as Terbinafine bind to and inhibit squalene epoxidase resulting in a block of ergosterol synthesis. These drugs are very potent against *Dermatophytes* while their activity against *Candida* species is very poor. In some cases treatment with allylamines is followed by severe cutaneous adverse reactions. A recent multinational case-control study (euroSCAR) (Sidoroff A. et al, *Br. J. Dermatol.*, 2007; 15, 989-996) revealed that Terbinafine systemic treatment is strongly associated with the development of an acute generalized exanthematous pustolosis (AGEP). This disease is characterized by the rapid occurrence of many sterile, non-follicular pustules, usually accompanied by leucocytosis and fever. AGEP is generally attributed to the patient treatment with particular drugs and seems to be related to an altered T cells activity. Terbinafine treatment might also induce dermatomyositis, a severe autoimmune connective tissue disease characterized by erythema, muscle weakness and interstitial pulmonary fibrosis (Magro C. M. et al, *J. Cutan. Pathol.*, 2008; 35, 74-81). In addition, as a variety of antifungal medications, Terbinafine might cause severe liver injuries (Perveze Z. et al, *Liver Transpl.*, 2007; 13, 162-164).

Griseofulvin is a benzofurane introduced in 1960 for the treatment of dermatophyte infections. The compound induces its fungistatic activity by interfering with microtubule production. Griseofulvin displays limited activity in the treatment of onychomycoses and frequently causes severe side effects such as nausea, diarrhea, headache, confusion and fatigue (Korting H. C. et al, *Antimicrob. Agents Chemother.*, 1993; 37, 2064-2068) that can cause the treatment discontinuation.

The two N-Hydroxy pyridones, Ciclopirox olamine and Octopirox, seem to mainly act by chelating polyvalent cations, resulting in the inhibition of the metal-dependent enzymes. They are employed against different fungal infections but their use is limited to topical treatment.

The echinocandins (Caspofungin, Micafungin, Anidulafungin) are semi-synthetic lipo-peptides and are the most recently introduced antimycotic drugs. They act by non-competitively inhibiting β-(1-3)-Dglucan synthase, an enzyme essential for the maintenance of the cell wall and are mainly used for intravenous treatment of invasive candidiasis and aspergillosis. They are fungicidal against yeast but only fungistatic against filamentous fungi; in addition, they are quite inactive against dimorphic fungi such as *Blastomyces* and *Histoplasma*. Echinocandins are generally well tolerated but animal reproduction studies showed adverse effects on fetus. For this reason FDA lists echinocandins as a pregnancy-risk category C (http://www.fda.gov/medwatch/SAFETY/2004/mar_PI/Cancidas_PI. pdf; http://www.fda.gov/medwatch/safety/2007/Aug_PI/Mycamine_PI.pdf).

EP1375486 discloses a generic and very broad class of compounds having HIV integrase inhibitory activity. This broad generic class includes 8-hydroxy-quinoline derivatives substituted by a wide variety of substituents, e.g., substituted carboxamide groups at the 7-position. None of the specific compounds disclosed in this reference are structurally similar to the compounds of the present invention.

EP1541558 discloses a generic and very broad class of compounds having HIV integrase inhibitory activity. As a matter of fact, the specific compounds disclosed in this reference always bear a substituent on the pyridyl ring and preferably are 3-(4-fluorobenzyl)-8-hydroxyquinolines. None of the specific compounds disclosed in this reference are structurally similar to the compounds of the present invention.

WO98/11073 (U.S. Pat. No. 6,310,211) discloses a generic class of anti-viral compounds having HIV integrase inhibitory activity. None of the specific compounds disclosed in this reference are structurally similar to the compounds of the present invention.

WO02/30426 discloses a generic class of compounds having HIV integrase inhibitory activity. As a matter of fact, most of the specific compounds disclosed in this reference bear a naphthydrinyl residue. None of the specific compounds disclosed in this reference are structurally similar to the compounds of the present invention.

WO02/30930 discloses a generic and very broad class of compounds having HIV integrase inhibitory activity. None of the specific compounds disclosed in this reference are structurally similar to the compounds of the present invention.

US0326330 and US0326328 disclose fungicidal compositions comprising a combination of two fungicides, one of which is a quinoline or cinnoline compound. None of the specific compounds disclosed in this reference are structurally similar to the compounds of the present invention.

WO96/32015 discloses synergistic fungicidal compositions made of quinoline derivatives and cytochrome complex III inhibitors. None of the specific compounds disclosed in this reference are structurally similar to the compounds of the present invention.

U.S. Pat. No. 6,194,413 discloses picolinoyl derivatives which are reported to be useful for treating viral, fungal or bacterial infections.

EP1669348 discloses antifungal agents defined by a very broad formula which includes certain secondary amides.

From what described above, it is evident that the clinical need for efficacious antifungal drugs has dramatically increased in the few last years. Unfortunately the currently available drugs, such as those disclosed in the above cited references, are not satisfactory, due to their narrow spectrum of action, pharmacokinetic properties and severe side effects.

DESCRIPTION OF THE INVENTION

The present invention particularly provides compounds of general formula (I), endowed with a potent antifungal activity

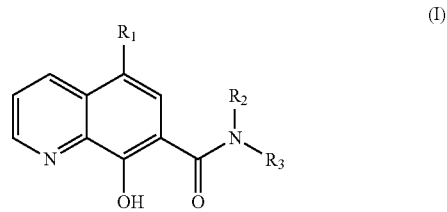

(I)

wherein $R_1$ is:
a) —H,
b) —F,
c) —Cl,
d) —Br,
e) —$NO_2$,
f) —$CF_3$,
g) —$C_1$-$C_6$ alkyl,
h) —(X)—$NR_4R_5$,
i) —CN,
j) —(Y)—$R_6$,
k) —$(CH_2)_n$-aryl, optionally substituted, or
l) —$(CH_2)_n$-heterocyclic, optionally substituted;
wherein X is:
a) —$(CH_2)_n$—,
b) —($SO_2$)—,
c) —(C=O)—, or
d) —(N—C=O)—;
wherein Y is:
a) —O—,
b) —S—,
c) —($SO_2$)—,
d) —($SO_3$)—,
e) —(C=O)—,
f) —($CO_2$)—,
g) —($CH_2O$)—, or
h) —($NHSO_2$)—;

wherein R$_2$ and R$_3$, independently from each other, are selected from:
   a) —C$_1$-C$_6$ alkyl, with the proviso that R$_2$ and R$_3$ are not both methyl,
   b) —(CH$_2$)$_n$-aryl, optionally substituted,
   c) —(CH$_2$)$_n$-cycloalkyl, optionally substituted,
   d) —(CH$_2$)$_n$-heterocycle, optionally substituted,
   e) —(CH$_2$)$_n$—OR$_6$,
   f) —(CH$_2$)$_n$—CN,
   g) —(CH$_2$)$_n$—NR$_4$R$_6$,
   h) taken together with the nitrogen atom to which they are bound to form an optionally substituted 5- to 8-membered heteromonocycle containing from one to three heteroatoms selected from the group consisting of oxygen and sulphur, or
   i) taken together with the nitrogen atom to which they are bound to form an optionally substituted 5- to 8-membered heteromonocycle which is fused to one or two optionally substituted saturated or unsaturated rings or to other heterocycles containing from one to three heteroatoms selected from the group consisting of nitrogen, oxygen and sulphur;
wherein R$_4$ and R$_5$, independently from each other, are selected from:
   a) —H,
   b) —C$_1$-C$_6$ alkyl,
   c) —(CH$_2$)$_n$-aryl, optionally substituted,
   d) —(CH$_2$)$_n$-cycloalkyl, optionally substituted,
   e) —(CH$_2$)$_n$-heterocycle, optionally substituted,
   f) —(CH$_2$)$_n$—OR$_6$,
   g) —(CH$_2$)$_n$—CN,
   h) taken together with the nitrogen atom to which they are bound to form an optionally substituted 5- to 8-membered heteromonocycle containing from one to three heteroatoms selected from the group consisting of nitrogen, oxygen and sulphur, or
   j) taken together with the nitrogen atom to which they are bound to form an optionally substituted 5- to 8-membered heteromonocycle which is fused to one or two optionally substituted saturated or unsaturated rings or to other optionally substituted heterocycles containing from one to three heteroatoms selected from the group consisting of nitrogen, oxygen and sulphur;
wherein R$_6$ is:
   a) —H,
   b) —C$_1$-C$_6$ alkyl,
   c) —(CH$_2$)$_n$-aryl, optionally substituted,
   d) —(CH$_2$)$_n$-cycloalkyl, optionally substituted, or
   e) —(CH$_2$)$_n$-heterocycle, optionally substituted;
wherein n is an integer from 0 to 6;
or pharmaceutically acceptable salts and derivatives thereof.

As used herein, the term "C$_1$-C$_6$ alkyl" means linear or branched chain alkyl groups having from 1 to 6 carbon atoms and includes all of the hexyl and pentyl alkyl isomers as well as n-, iso-, sec- and t-butyl, n- and isopropyl, ethyl and methyl.

The term "cycloalkyl" means a cyclic ring of an alkane selected from cyclopropyl, cyclobutyl, cyclopentyl, cyclohexyl, cycloheptyl and cyclooctyl.

The term "aryl" refers to aromatic mono- and poly-carbocyclic ring systems, wherein the individual carbocyclic rings in the polyring systems may be fused or attached to each other via a single bond. Suitable aryl groups include, but are not limited to, phenyl, naphthyl and biphenyl.

The term "heterocycle" (and variations thereof such as "heterocyclic") broadly refers to a 4- to 8-membered monocyclic rings, 7- to 12-membered bicyclic ring systems or an 11- to 16-membered tricyclic ring system, any ring of which is saturated or unsaturated, and which consists of carbon atoms and one or more heteroatoms selected from N, O and S, and wherein the nitrogen and sulphur heteroatoms may optionally be oxidized and the nitrogen heteroatom may optionally be quaternized. The hetorocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results.

The term "heteromonocycle" (and variations thereof such as "heteromonocyclic") refers to a 4- to 8-membered monocyclic ring which is saturated or unsaturated, and which consists of carbon atoms and one or more heteroatoms selected from N, O and S, and wherein the nitrogen and sulphur heteroatoms may optionally be oxidized, and the nitrogen heteroatom may optionally be quaternized. The heterocycle ring may be attached at any heteroatom or carbon atom, provided that attachment results in the creation of a stable structure. When the heterocycle ring is an aromatic heterocycle ring it can be defined "heteroaromatic ring".

Unless expressly set forth to the contrary, an "unsaturated" ring is a partially or fully unsaturated ring. For example, an "unsaturated monocyclic C$_6$ carbocycle" refers to cyclohexene, cyclohexadiene and benzene.

The term "substituted" includes mono- and poly-substitution by a named substituent to the extent such single and multiple substitution is chemically allowed. For example, a carbocycle or heterocycle substituted with more than one substituent can have multiple substituents on the same ring atom to the extent it is chemically permitted. A ring sulphur atom in a saturated heterocycle can, for example, typically be substituted with one (—S(=O)—) or two oxo groups (—SO$_2$—).

"Pharmaceutically acceptable salts or derivatives" refers to those salts or derivatives which possess the biological effectiveness and properties of the parent compound and which are not biologically or otherwise undesirable. Such salts include those with inorganic or organic acids, as for instance, the hydrobromide, hydrochloride, sulfate, phosphate, sodium salt, magnesium salt; such derivatives include the esters, the ethers and the N-oxides.

The compounds of the present invention and their pharmaceutical acceptable salts or derivatives may have asymmetric centres and may occur, except when specifically noted, as mixtures of stereoisomers or as individual diastereomers, or enantiomers, with all isomeric forms being included in the present invention.

The phrase "pharmaceutically acceptable", as used in connection with the formulations containing the compounds of the invention, refers to molecular entities and other ingredients of such formulations that are physiologically tolerable and do not typically produce untoward reactions when administered to an animal such as a mammal (e.g., a human). Preferably, as used herein, the term "pharmaceutically acceptable" means approved by a regulatory agency, such as the FDA or the EMEA, or listed in the U.S. or European Pharmacopeia or other generally recognized pharmacopeia for use in mammals, and more particularly in humans.

Preferably in formula (I):
   R$_1$ is:
   a) —H,
   b) —Br, or
   c) —NO$_2$;

$R_2$ and $R_3$, independently from each other, are selected from:
a) —$C_1$-$C_6$ alkyl, with the proviso that $R_2$ and $R_3$ are not both methyl,
b) —$(CH_2)_n$-aryl, optionally substituted,
c) —$(CH_2)_n$-cycloalkyl, optionally substituted,
d) —$(CH_2)_n$-heterocycle, optionally substituted,
e) —$(CH_2)_n$—$OR_6$,
f) —$(CH_2)_n$—CN,
g) taken together with the nitrogen atom to which they are bound to form an optionally substituted 5- to 8-membered heteromonocycle containing from one to three heteroatoms selected from the group consisting of oxygen and sulphur, or
h) taken together with the nitrogen atom to which they are bound to form an optionally substituted 5- to 8-membered heteromonocycle which is fused to one or two optionally substituted unsaturated or saturated rings or to other heterocycles containing from one to three heteroatoms selected from the group consisting of nitrogen, oxygen and sulphur;
$R_6$ is H;
and/or n is an integer from 0 to 6, preferably from 0 to 2.
Further preferably in formula (I):
$R_1$ is H;
$R_2$ and $R_3$ are different from H and are, independently:
a) —$C_1$-$C_6$ alkyl, with the proviso that $R_2$ and $R_3$ are not both methyl,
b) —$(CH_2)_n$-aryl, optionally substituted, or
c) taken together with the nitrogen atom to which they are bound to form an optionally substituted 5- to 8-membered heteromonocycle which is fused to one or two optionally substituted unsaturated or saturated rings or to other heterocycles containing from one to three heteroatoms selected from the group consisting of nitrogen, oxygen and sulphur;
and/or n is an integer from 0 to 6, preferably from 0 to 2.

According to a preferred embodiment of the invention, $R_2$ is different from $R_3$. Preferred compounds of the invention include, but are not limited to, compounds selected from the group consisting of:
8-Hydroxy-N-methyl-N-(4-(2-phenylpropan-2-yl)benzyl) quinoline-2-carboxamide;
N-Benzyl-8-hydroxy-N-methylquinoline-7-carboxamide;
(8-Hydroxyquinolin-7-yl)(isoindolin-2-yl)methanone;
(8-Hydroxyquinolin-7-yl)(morpholino)methanone;
(8-Hydroxyquinolin-7-yl)(piperidin-1-yl)methanone;
8-Hydroxy-N-methyl-N-phenethylquinoline-7-carboxamide;
(8-Hydroxyquinolin-7-yl)(indolin-1-yl)methanone;
N-(Furan-2-ylmethyl)-8-hydroxy-N-methylquinoline-7-carboxamide;
(3,4-Dihydroquinolin-1(2H)-yl)(8-hydroxyquinolin-7-yl)methanone;
N-(4-Bromobenzyl)-8-hydroxy-N-methylquinoline-7-carboxamide;
8-Hydroxy-N-(4-methoxyphenyl)-N-methylquinoline-7-carboxamide;
(6,7-Dimethoxy-3,4-dihydroisoquinolin-2(1H)-yl)(8-hydroxyquinolin-7-yl)methanone;
8-Hydroxy-N-methyl-N-(tetrahydro-2H-pyran-4-yl)quinoline-7-carboxamide;
8-Hydroxy-N-methyl-N-phenylquinoline-7-carboxamide;
N-(4-Chlorophenyl)-8-hydroxy-N-methylquinoline-7-carboxamide;
N-Ethyl-8-hydroxy-N-phenylquinoline-7-carboxamide;
N-Cyclohexyl-8-hydroxy-N-methylquinoline-7-carboxamide;
8-Hydroxy-N-methyl-N-(1-methylpiperidin-4-yl)quinoline-7-carboxamide;
8-Hydroxy-N-methyl-N-(1-methylpyrrolidin-3-yl)quinoline-7-carboxamide;
N-(2-Cyanoethyl)-N-(furan-2-ylmethyl)-8-hydroxyquinoline-7-carboxamide;
N-(2-Cyanoethyl)-8-hydroxy-N-((tetrahydrofuran-2-yl)methyl)quinoline-7-carboxamide;
N-Ethyl-8-hydroxy-N-methylquinoline-7-carboxamide;
8-Hydroxy-N-methyl-N-propylquinoline-7-carboxamide;
(3,4-Dihydroisoquinolin-2(1H)-yl)(8-hydroxyquinolin-7-yl)methanone;
(5-Bromoindolin-1-yl)(8-hydroxyquinolin-7-yl)methanone;
(8-Hydroxyquinolin-7-yl)(6-methoxy-3,4-dihydroquinolin-1(2H)-yl)methanone;
(8-Hydroxyquinolin-7-yl)(5-nitroindolin-1-yl)methanone;
8-Hydroxy-N-phenyl-N-propylquinoline-7-carboxamide;
(8-Hydroxyquinolin-7-yl)(octahydroquinolin-1(2H)-yl)methanone;
N-(4-Fluorobenzyl)-8-hydroxy-N-methylquinoline-7-carboxamide;
N-(3-Bromobenzyl)-8-hydroxy-N-methylquinoline-7-carboxamide;
(8-Hydroxyquinolin-7-yl)(4-(trifluoromethyl)piperidin-1-yl)methanone;
(4-tert-Butylpiperidin-1-yl)(8-hydroxyquinolin-7-yl)methanone;
(S)-8-Hydroxy-N-methyl-N-(1-phenylethyl)quinoline-7-carboxamide;
N-Benzyl-8-hydroxy-N-(2-hydroxyethyl)quinoline-7-carboxamide;
(3,3-Dimethylpiperidin-1-yl)(8-hydroxyquinolin-7-yl)methanone;
N-(2-Bromobenzyl)-8-hydroxy-N-methylquinoline-7-carboxamide;
(8-Hydroxyquinolin-7-yl)(4-phenylpiperidin-1-yl)methanone;
((4aS,8S,8aR)-8-Hydroxy-octahydroquinolin-1(2H)-yl)(8-hydroxyquinolin-7-yl)methanone;
(8-Hydroxyquinolin-7-yl)(2-methylpiperidin-1-yl)methanone;
(8-Hydroxyquinolin-7-yl)(2-phenylpiperidin-1-yl)methanone;
(1,1-Dioxo-thiomorpholin-4-yl)-(8-hydroxy-quinolin-7-yl)-methanone;
(8-Hydroxyquinolin-7-yl)(4-methylpiperidin-1-yl)methanone;
(R)-8-Hydroxy-N-(1-phenylethyl)quinoline-7-carboxamide;
(8-Hydroxyquinolin-7-yl)(2-methylpyrrolidin-1-yl)methanone;
(2,5-Dimethylpyrrolidin-1-yl)(8-hydroxyquinolin-7-yl)methanone;
(8-Hydroxyquinolin-7-yl)(3-phenylpyrrolidin-1-yl)methanone;
(3-(Dimethylamino)pyrrolidin-1-yl)(8-hydroxyquinolin-7-yl)methanone;
(8-Hydroxyquinolin-7-yl)(3-methylpiperidin-1-yl)methanone;
(8-Hydroxyquinolin-7-yl)(pyrrolidin-1-yl)methanone;
(1,4-Dioxa-8-aza-spiro[4.5]dec-8-yl)-(8-hydroxy-quinolin-7-yl)-methanone;

(8-Hydroxyquinolin-7-yl)(6-methyl-3,4-dihydroquinolin-1 (2H)-yl)methanone;

(8-Hydroxyquinolin-7-yl)(6-nitroindolin-1-yl)methanone;

(8-Hydroxyquinolin-7-yl)(7-(trifluoromethyl)-3,4-dihydroquinolin-1(2H)-yl)methanone;

(5-Bromo-8-hydroxyquinolin-7-yl)(isoindolin-2-yl)methanone;

(Hexahydro-1H-isoindol-2(3H)-yl)(8-hydroxyquinolin-7-yl)methanone;

(8-Hydroxyquinolin-7-yl)(2-methyl-3,4-dihydroquinolin-1 (2H)-yl)methanone;

(8-Hydroxyquinolin-7-yl)(3-methyl-3,4-dihydroquinolin-1 (2H)-yl)methanone;

(8-Hydroxyquinolin-7-yl)(4-methyl-3,4-dihydroquinolin-1 (2H)-yl)methanone;

(8-Fluoro-3,4-dihydroquinolin-1(2H)-yl)(8-hydroxyquinolin-7-yl)methanone;

(8-Hydroxyquinolin-7-yl)(6-isopropyl-3,4-dihydroquinolin-1(2H)-yl)methanone;

(6-Chloro-3,4-dihydroquinolin-1(2H)-yl)(8-hydroxyquinolin-7-yl)methanone;

(8-Hydroxyquinolin-7-yl)(7-methyl-3,4-dihydroquinolin-1 (2H)-yl)methanone;

(6-Bromo-3,4-dihydroquinolin-1(2H)-yl)(8-hydroxyquinolin-7-yl)methanone;

(2H-Benzo[b][1,4]oxazin-4(3H)-yl)(8-hydroxyquinolin-7-yl)methanone.

In a particularly preferred embodiment, the compounds of the present invention are selected from:

(8-Hydroxyquinolin-7-yl)(isoindolin-2-yl)methanone (Example 10);

(8-Hydroxyquinolin-7-yl)(octahydroisoquinolin-2(1H)-yl) methanone (Example 6);

N-(4-Bromophenyl)-8-hydroxy-N-methylquinoline-7-carboxamide (Example 29);

(Decahydro-1H-carbazol-9(9aH)-yl)(8-hydroxyquinolin-7-yl)methanone (Example 49);

N-(4-Chlorobenzyl)-8-hydroxy-N-methylquinoline-7-carboxamide (Example 56);

(5,7-Difluoro-3,4-dihydroquinolin-1(2H)-yl)(8-hydroxyquinolin-7-yl)methanone (Example 70);

(7-Fluoro-3,4-dihydroquinolin-1(2H)-yl)(8-hydroxyquinolin-7-yl)methanone (Example 61);

(5-Fluoro-3,4-dihydroquinolin-1(2H)-yl)(8-hydroxyquinolin-7-yl)methanone (Example 71);

(6-Fluoro-3,4-dihydroquinolin-1(2H)-yl)(8-hydroxyquinolin-7-yl)methanone (Example 72);

(5-Chloro-8-hydroxy-3,4-dihydroquinolin-1(2H)-yl)(8-hydroxyquinolin-7-yl)methanone (Example 73);

(2H-Benzo[b][1,4]oxazin-4(3H)-yl)(8-hydroxyquinolin-7-yl)methanone (Example 74).

The compounds of the present invention can be prepared by the coupling of suitable 8-hydroxyquinolin-7-carboxylic acids 1-1 (or acid derivatives such as acid halides or esters) with the appropriate amines 1-2, as represented by the following general Chart 1:

CHART 1

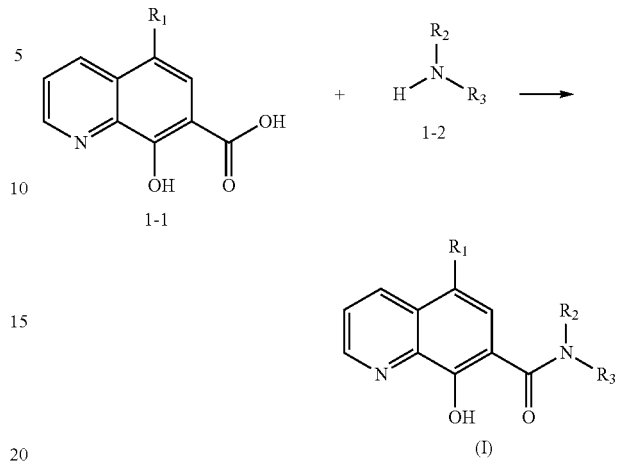

Alternatively the hydroxyl group of the carboxylic acid can be protected (as described in *Bioorg. Med. Chem.*, 14, 2006, 5742-5755 or *Synthesis*, 12, 1997, 1425-1428 or DE540842) before performing the coupling with the amine and deprotected in the final stage.

Methods for coupling carboxylic acids with amines to form carboxamides are well known in the art. Suitable methods are described, for example, in Jerry March, *Advanced Organic Chemistry*, 4th edition, John Wiley & Sons, 1992, pp. 417-425.

Methods for protecting and deprotecting aromatic hydroxyl groups are well known in the art. Protecting groups are manipulated according to standard methods of organic synthesis (Green T. W. and Wuts P. G. M. (1991) *Protecting Groups in Organic Synthesis*, John Wiley et Sons).

Charts 2-3 below illustrate and expand upon the chemistry portrayed in Chart 1.

CHART 2

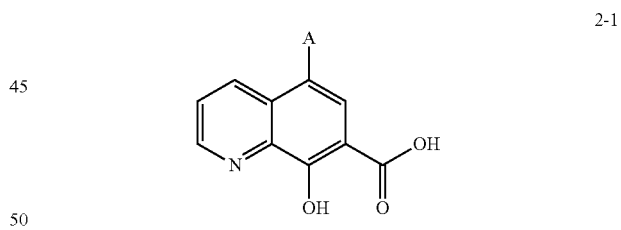

When A is Br, carboxylic acid 2-1 (which is prepared in Preparation 4 below) was obtained by reaction of commercially available 8-hydroxyquinoline-7-carboxylic acid with one equivalent of bromine in acetic acid (International Publication WO98/11073, published 19 Mar. 1998).

When A is F or Cl, carboxylic acids 2-1 can be prepared from the corresponding commercially available starting materials 5-halo-8-hydroxyquinolines using the methods described in International Publication WO98/11073, published 19 Mar. 1998.

When A is $NO_2$ carboxylic acid 2-1 was prepared by reaction of the corresponding ethyl ester with a mixture of $HNO_3$ and $H_2SO_4$ followed by alkaline hydrolysis. Alternatively, carboxylic acid 2-1 with A=$NO_2$ was prepared by reaction of 3-amino-2-hydroxy-5-nitrobenzoic acid with propenal in 6N HCl Compounds of general formula I-2 of Chart 1 are commercially available or were prepared using conventional synthetic procedures well known to those skilled in the art. When 1-2 were tetrahydroquinolines (3-2) not commercially available, they were obtained by reduction of the corresponding quinolines 3-1 by using conventional synthetic procedures such as with platinum oxide and $H_2$ or with Zn and hydrochloric acid.

CHART 3

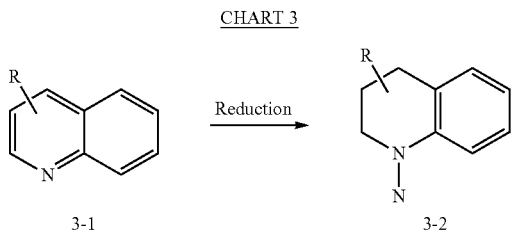

Preparation of suitable substituted not commercially available quinolines 3-1 was accomplished by using conventional synthetic procedures, not mentioned in greater details. In these reactions, it is also possible to make use of variants which are themselves known to those of ordinary skill in this art.

It will be apparent to those skilled in the art that the described synthetic procedures are merely representative in nature and that alternative synthetic processes are known to one of ordinary skill in organic chemistry.

The following examples serve only to illustrate the invention and its practice. The examples are not to be constructed as limitation on the scope or spirit of the invention.

EXPERIMENTAL SECTION

1. Chemical Synthesis

Unless otherwise indicated, all the starting reagents were found to be commercially available and were used without any prior purification. The compounds of the present invention can be readily prepared using conventional synthetic procedure. In these reactions, it is also possible to make use of variants which are themselves known to those of ordinary skill in this art, but are not mentioned in greater detail. Furthermore, other methods for preparing compounds of this invention will be readily apparent to the person of ordinary skill in the art in light of the following reaction schemes and examples. Unless otherwise indicated, all variables are as defined above. Where reference is made to the use of an "analogous" procedure, as will be appreciated by those skilled in the art, such a procedure may involve minor variation, for example reaction temperature, reagent/solvent amount, reaction time, work-up conditions or chromatographic purification conditions. Abbreviations used in the instant specification, particularly in the Tables and in the Examples, are summarized in Table 1.

TABLE 1

| | |
|---|---|
| UPLC (Ultra Performance Liquid Chromatography) | $R_t$ (retention time in minutes) |
| LC-MS (Liquid Chromatography Mass Spectrum) | ESI (Electro Spray Ionization) |
| | min (minutes) |
| HPLC (High Performance Liquid Chromatography) | h (hours) |
| | μL (microlitres) |
| CH$_3$CN (Acetonitrile) | TFA (Trifluoroacetic acid) |
| μm (micrometers) | Pd/C (palladium on carbon) |
| | MW (microwave) |

TABLE 1-continued

| | |
|---|---|
| mmol (millimoles) | HOBt (1-Hydroxybenzotriazole) |
| psi (pound per square inch) | THF (Tetrahydrofuran) |
| RT (room temperature) | DIPEA (N,N-Diisopropilethylamine) |
| SPE-SI (Solid phase extraction with Silica gel) | NaOH (Sodium hydroxide) |
| | LiAlH$_4$ (Litium aluminnium hydride) |
| DCM (Dichloromethane) | NaBH$_4$ (Sodium borohydride) |
| K$_2$CO$_3$ (Potassium carbonate) | HCl (Hydrochloric acid) |
| Na$_2$SO$_4$ (Sodium sulphate) | MeOH (Methanol) |
| Et$_2$O (Diethyl ether) | CFU (Colony Forming Unit) |
| EtOAc (Ethyl acetate) | |
| TEA (Triethylamine) | |
| i-PrOH (Isopropyl alcohol) | |
| DMSO (Dimethyl sulfoxide) | |
| EDC•HCl (1-(3-Dimethylaminopropyl)-3-ethylcarbodiimide hydrochloride)) | |

Except where otherwise indicated, all temperatures are expressed in ° C. (degrees centigrade) or K (Kelvin).

Proton Nuclear Magnetic Resonance ($^1$H-NMR) spectra were recorded on a Brucker 300 MHz. Chemical shifts are expressed in parts of million (ppm, δ units). Splitting patterns describe apparent multiplicities and are designated as s (singlet), d (doublet), t (triplet), q (quartet), quint (quintet), sxt (sextet), m (multiplet), br. s (broad singlet).

LC-MS were recorded under the following conditions:

Method A-C: UPLC with Sample Manager and 2996 PDA Detector (Waters) interfaced with a Mass Spectrometer Single Quadrupole ZQ (Waters). ZQ interface: ESI positive mode. Full scan from 102 to 900 amu. Capillary 3.2V, cone 25V, extractor 3V, RF 0.3V, source temperature 115° C., desolvation temperature 350° C., gas flow 800 L/h, cone 100 L/h. Column Aquity UPLC-BEH C18 (50×2.1 mm, 1.7 μm). Flow rate 0.6 mL/min, column at 40° C., injection 2 μL. Mobile phases: A phase=water/CH$_3$CN 95/5+0.1% TFA, B phase=water/CH$_3$CN=5/95+0.1% TFA.

Method A: 0-0.25 min (A: 95%, B: 5%), 3.30 min (A: 0%, B: 100%), 3.30-4.00 (A: 0%, B: 100%), 4.10 min (A: 95%, B: 5%), 4.10-5.00 min (A: 95%, B: 5%).

Method B: 0-1.00 min (A: 100%, B: 0%), 1.50 min (A: 95%, B: 5%), 3.50 min (A: 0%, B: 100%), 3.50-4.00 (A: 0%, B: 100%), 4.10 min (A: 100%, B: 0%), 4.10-5.00 min (A: 100%, B: 0%).

Method C: 0-0.50 min (A: 95%, B: 5%), 6.00 min (A: 0%, B: 100%), 6.00-7.00 (A: 0%, B: 100%), 7.10 min (A: 95%, B: 5%), 7.10-8.50 min (A: 95%, B: 5%).

Method D: Waters 1525 HPLC pump (Waters) and 2996 PDA detector (Waters) interfaced with a Mass Spectrometer Single Quadrupole ZQ (Waters). ZQ interface: ESI positive mode. Full scan from 102 to 900 amu. Capillary 3.2V, cone 25V, extractor 3V, RF 0.3V, source temperature 115° C., desolvation temperature 350° C., gas flow 600 L/h, cone 100 L/h. Column X-bridge C18 (50×2.1 mm, 3.5 μm). Flow rate 0.4 mL/min, column at 40° C., injection 5 μL. Mobile phases: A phase=water/CH$_3$CN 95/5+NH$_3$ pH 9.5, B phase=water/CH$_3$CN=5/95+NH$_3$ pH 9.5.0-1.00 min (A: 95%, B: 5%), 7.50 min (A: 0%, B: 100%), 7.50-8.50 min (A: 0%, B: 100%), 8.60 min (A: 95%, B: 5%), 8.60-9.60 min (A: 95%, B: 5%).

Method E: UPLC with Sample Manager and 2996 PDA Detector (Waters) interfaced with a Mass Spectrometer Single Quadrupole ZQ (Waters). ZQ interface: ESI positive mode. Full scan from 100 to 600 amu. Capillary 3.25V, cone 26V, extractor 3V, source temperature 120° C., desolvation temperature 400° C., gas flow 800 L/h, cone 100 L/h. Column Aquity UPLC-BEH C18 (50×2.1 mm, 1.7 μm). Flow rate 0.5 mL/min, column at 40° C., injection 2 μL. Mobile phases: A phase=water/CH$_3$CN 95/5+0.1% TFA, B phase=water/CH$_3$CN=5/95+0.1% TFA. 0 min (A: 95%, B: 5%), 0.30 min (A: 92%, B: 8%), 1.50 min (A: 0%, B: 100%), 1.50-2.00 min (A: 0%, B: 100%).

Method F: Waters 1525 HPLC pump (Waters) and 2996 PDA detector (Waters) interfaced with a Mass Spectrometer Single Quadrupole ZQ (Waters). ZQ interface: ESI positive mode. Full scan from 102 to 900 amu. Capillary 3.2V, cone 25V, extractor 3V, RF 0.3V, source temperature 115° C., desolvation temperature 350° C., gas flow 600 L/h, cone 100 L/h. Column Synergy C18 (20×2.0 mm, 2.5 μm). Flow rate 0.7 mL/min, injection 2 μL. Mobile phases: A phase=water/CH$_3$CN 95/5+TFA 0.1%, B phase=water/CH$_3$CN=5/95+TFA 0.1%. 0-0.25 min (A: 95%, B: 5%), 3.50 min (A: 0%, B: 100%), 3.50-4.50 min (A: 0%, B: 100%), 4.60 min (A: 95%, B: 5%), 4.60-6.00 min (A: 95%, B: 5%).

Software, Columns and Conditions Used for Preparative HPLC Purification Software Shimadzu CLASS-VP 1.0.0.1

Column

The column used is a Waters Symmetry Prep C18 column whose dimensions are 19 mm internal diameter by 300 mm in length. The stationary phase particle size is 7 μm. Solvents A. Aqueous solvent=water/CH$_3$CN 90/10+0.05% TFA.

B. Organic solvent=CH$_3$CN/water 90/10+0.05% TFA.

Needle rinse solvent=i-PrOH.

Method

Only one method was used (5-100% B); it has a flow rate of 20 mL/min and a 35-minute runtime, which comprises of a 28-minute gradient followed by a 7-minute column flush and re-equilibration step.

Preparation 1

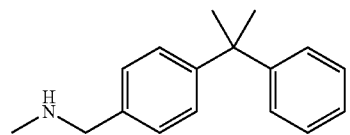 [SMILES: CNCc1ccc(C(C)(C)c2ccccc2)cc1]

N-Methyl-1-(4-(2-phenylpropan-2-yl)phenyl)methanamine hydrochloride

Step A: 4-(2-Phenylpropan-2-yl)benzaldehyde

A suspension of propane-2,2-diyldibenzene (3.93 g, 20 mmol) and 1-aza-tricyclo[3.3.1.1*3,7*]decane (2.80 g, 20 mmol) in TFA (35 mL) was heated at 100° C. for 16 h. The reaction mixture was allowed to cool to RT, poured onto cold water and made alkaline (pH=9) with solid K$_2$CO$_3$. The aqueous solution was extracted with Et$_2$O (3×250 mL) and the separated organics were dried over Na$_2$SO$_4$, filtered and concentrated under reduced pressure. The residue was purified by flash chromatography (silica gel, petroleum ether:EtOAc 95:5) affording the title compound (3.47 g, 15.46 mmol).

$^1$H-NMR (CDCl$_3$) δ: 10.00 (s, 1H); 7.81 (m, 2H); 7.42 (m, 2H); 7.14-7.38 (m, 5H); 1.74 (s, 6H).

Step B: N-Methyl-1-(4-(2-phenylpropan-2-yl)phenyl)methanamine hydrochloride

A 10M solution of methylamine in ethanol (4 mL, 40 mmol) was added to a solution of 4-(2-phenylpropan-2-yl) benzaldehyde (2.24 g, 10 mmol) of Preparation 1 in absolute ethanol (30 mL) and the resulting mixture was stirred at RT, under nitrogen, overnight. The reaction mixture was then filtered through a CELITE pad and the liquids concentrated under reduced pressure. The residue was dissolved in dry methanol (25 mL) and treated portion wise, at 0° C., with NaBH$_4$ (456 mg, 12 mmol). After completion of the addition the reaction mixture was heated to 40° C. for 1 h and then stirred at RT, under nitrogen, overnight. The reaction mixture was quenched with H$_2$O and concentrated under reduced pressure. The residue was partitioned between H$_2$O and Et$_2$O and the separated organics were dried over Na$_2$SO$_4$, filtered and concentrated to dryness. The residue was then dissolved in absolute ethanol, a 4N solution of HCl in dioxane (4 mL) was added and the mixture was stirred at RT overnight. The mixture was concentrated under reduced pressure and the obtained residue was triturated with iPrOH, affording the title compound (1.71 g, 7.15 mmol).

$^1$H-NMR (DMSO-d$_6$) δ: 9.25 (br. s, 2H); 7.44 (m, 2H); 7.10-7.36 (m, 7H); 4.04 (t, 2H); 2.51-2.57 (m, 3H); 1.65 (s, 6H).

Preparation 2

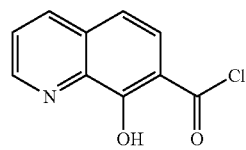 [SMILES: O=C(Cl)c1ccc2cccnc2c1O]

8-Hydroxyquinoline-7-carbonyl chloride

Thionyl chloride (906 mg, 7.61 mmol) was added drop wise to a cold solution of 8-hydroxyquinoline-7-carboxylic acid (1.2 g, 6.34 mmol) in dry DCM (18 mL). The reaction mixture was allowed to warm to RT and was then stirred under nitrogen for 4 h. The reaction mixture was then concentrated to dryness affording the title compound (1.3 g, 6.26 mmol) that was used in the next steps without any further purification.

Preparation 3

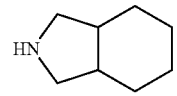

Octahydro-1H-isoindole

Step A: Hexahydro-1H-isoindole-1,3(2H)-dione

A solution of (3aR,7aS)-3a,4,7,7a-tetrahydro-1H-isoindole-1,3(2H)-dione (3.0 g, 19.9 mmol) and 10% Pd/C (300 mg) in MeOH (100 mL) was shaken in an H$_2$ atmosphere (300 psi) in a Parr apparatus for 24 h. The reaction mixture was filtrated and the liquids concentrated to dryness, affording the title compound (2.6 g, 16.99 mmol), that was sued without any further purification, as a white powder.

$^1$H-NMR (CDCl$_3$) δ: 8.16 (br. s, 1H); 2.73-3.05 (m, 2H); 1.64-1.98 (m, 4H), 1.40-1.64 (m, 4H).

Step B: Octahydro-1H-isoindole

A solution of hexahydro-1H-isoindole-1,3(2H)-dione (1.0 g, 6.5 mmol) in dry THF (14 mL) was added dropwise to a stirred slurry of LiAlH$_4$ in dry THF (6 mL) at such a rate that the solvent gentle refluxed. The resulting reaction mixture was heated to reflux for 20 h and then allowed to cool to RT. The reaction mixture was cooled with an ice-bath, and H$_2$O (1 mL), a 20% aqueous solution of NaOH (2.5 mL) and H$_2$O (2 mL) were sequentially added. The mixture was filtered and THF removed under reduced pressure. The aqueous phase was extracted with Et$_2$O, and the separated organics were dried over Na$_2$SO$_4$, filtered and concentrated to dryness, affording the title compound (690 mg, 5.52 mmol) as a white powder that was used in the next step without any further purification.

LC-MS m/z (ESI$^+$): 126.1 (MH$^+$), R$_t$=0.80 min (method E).

Preparation 4

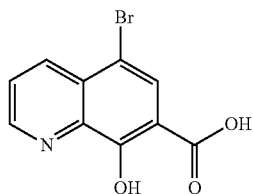 [SMILES: O=C(O)c1cc(Br)c2cccnc2c1O]

5-Bromo-8-hydroxyquinoline-7-carboxylic acid

Bromine (819.8 mg, 5.13 mmol) was added dropwise to a suspension of 8-hydroxyquinolin-7-carboxylic acid (970 mg, 5.13 mmol) in glacial acetic acid (24 mL). The reaction mixture was refluxed for 1 h, allowed to cool to 50° C. and poured onto ice water. The yellow solid formed was filtered on a Buckner funnel, washed with H$_2$O and dried under vacuum, affording the title compound (1.20 g, 4.51 mmol) as a light brown solid that was used in the next step without any further purification.

$^1$H-NMR (DMSO-d$_6$) δ: 9.90 (dd, 1H); 8.58 (dd, 2H); 8.12 (s, 1H); 7.90 (dd, 1H).

Example 1

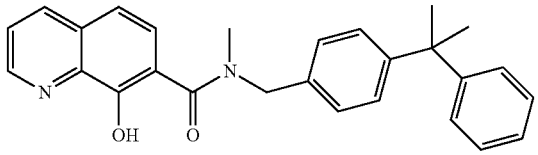 [SMILES: CN(Cc1ccc(C(C)(C)c2ccccc2)cc1)C(=O)c1ccc2cccnc2c1O]

8-Hydroxy-N-methyl-N-(4-(2-phenylpropan-2-yl)benzyl)quinoline-2-carboxamide

TEA (42 mg, 0.42 mmol), EDC.HCl (80 mg, 0.42 mmol), HOBt (57 mg, 0.418 mmol) and N-methyl-1-(4-(2-phenylpropan-2-yl)phenyl)methanamine (50 mg, 0.21 mmol) of Preparation 1 were sequentially added to a suspension of 8-hydroxyquinoline-7-carboxylic acid (48 mg, 0.25 mmol) in DCM (2.5 mL). The resulting reaction mixture was stirred at RT overnight. The mixture was quenched with H$_2$O and then extracted three times with DCM. The separated organics were dried over Na$_2$SO$_4$, filtered and concentrated under reduced pressure. The residue was purified by flash chromatography (silica gel, DCM:MeOH 95:5) affording the title compound (39 mg, 0.1 mmol) as a grey solid. LC-MS m/z (ESI$^+$): 411.2 (MH$^+$), R$_t$=2.42 min (Method A).

$^1$H-NMR (DMSO-d$_6$, 353K) δ: 8.89 (dd, 1H); 8.33 (dd, 1H); 7.59 (dd, 1H); 7.35-7.50 (m, 2H); 7.11-7.32 (m, 9H); 4.60 (s, 2H); 2.88 (s, 3H); 1.66 (s, 6H).

Following procedures analogous to the one described above, the additional compounds of the present invention were prepared (Table 2).

TABLE 2

| Ex. | Chemical name | $^1$H-NMR (DMSO-d$_6$) | LC-MS method | R$_t$ [MH$^+$] |
|---|---|---|---|---|
| 2 | N-Benzyl-8-hydroxy-N-methylquinoline-7-carboxamide | (+Na$_2$CO$_3$) δ: 8.48 (d, 1H); 7.97 (d, 1H); 6.78-7.73 (m, 7H); 6.49 (d, 1H); 4.64 (br. s, 2H); 2.89 (br. s, 3H) | A | 1.53; 293 |
| 3 | (8-Hydroxyquinolin-7-yl)(morpholino)methanone | δ: 10.26 (br. s, 1H); 8.91 (dd, 1H); 8.37 (dd, 1H); 7.62 (dd, 1H); 7.47 (d, 1H); 7.39 (d, 1H); 3.61 (br. s, 4H); 3.28 (br. s, 4H) | A | 0.76; 259.1 |

TABLE 2-continued

| Ex. | Chemical name | ¹H-NMR (DMSO-d₆) | LC-MS method | $R_t$ [MH⁺] |
|---|---|---|---|---|
| 4 | 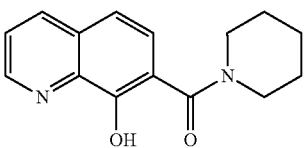<br>(8-Hydroxyquinolin-7-yl)(piperidin-1-yl)methanone | δ: 10.12 (br. s, 1H); 8.90 (dd, 1H); 8.36 (dd, 1H); 7.61 (dd, 1H); 7.45 (d, 1H); 7.35 (d, 1H); 3.27 (br. s, 4H); 1.12-1.98 (m, 6H) | A | 1.20; 257.2 |
| 5 | 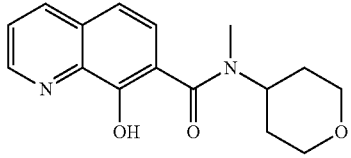<br>8-Hydroxy-N-methyl-N-(tetrahydro-2H-pyran-4-yl)quinoline-7-carboxamide | δ: 10.04 (br. s, 1H); 8.65-8.95 (m, 1H); 8.06-8.35 (m, 1H); 7.44-7.72 (m, 1H); 7.02-7.35 (m, 7H); 3.37 (s, 3H) | A | 1.34; 279.1 |

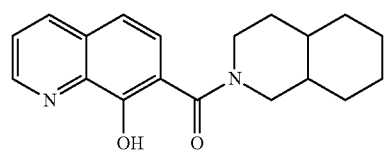 [SMILES: O=C(c1ccc2cccnc2c1O)N1CCC2CCCCC2C1]

(8-Hydroxyquinolin-7-yl)(octahydroisoquinolin-2(1H)-yl)methanone

A solution of 8-hydroxyquinoline-7-carbonyl chloride of Preparation 2 (70 mg, 0.35 mmol) and decahydroisoquinoline (62.6 mg, 0.45 mmol) in THF (8 mL) and DIPEA (259 mg, 2.0 mmol) was stirred and heated at 50° C. overnight. The reaction mixture was concentrated under reduced pressure and the residue was partitioned between DCM and H₂O. The separated organics were dried over Na₂SO₄, filtered and concentrated under reduced pressure. The residue was purified by flash chromatography (silica gel, DCM:MeOH 98:2) and then by preparative HPLC. Product-containing fractions were combined, made basic with a saturated aqueous solution of sodium hydrogen carbonate and CH₃CN was removed under reduced pressure. The aqueous phase was extracted with DCM and the separated organics dried over Na₂SO₄, filtered and concentrated to dryness, affording the title compound (49 mg, 0.16 mmol) as a off-white solid.

LC-MS m/z (ESI⁺): 311.2 (MH⁺), $R_t$=2.64-2.73 min (Method C).

¹H-NMR (DMSO-d₆, 353K) δ: 8.89 (dd, 1H); 8.33 (dd, 1H); 7.59 (dd, 1H); 7.44 (d, 1H); 7.35 (d, 1H); 3.56-4.22 (m, 2H); 3.24 (dd, 1H); 3.16 (ddd, 1H); 1.02-2.12 (m, 12H).

Following procedures analogous to the one described above, the additional compounds of the present invention were prepared (Table 3).

TABLE 3

| Ex. | Chemical name | ¹H-NMR (DMSO-d₆) | LC-MS method | $R_t$ [MH⁺] |
|---|---|---|---|---|
| 7 | 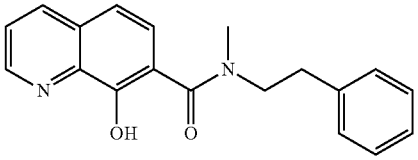 [SMILES: CN(CCc1ccccc1)C(=O)c1ccc2cccnc2c1O]<br>8-Hydroxy-N-methyl-N-phenethylquinoline-7-carboxamide | δ: 8.90 (dd, 1H); 8.33 (dd, 1H); 7.59 (dd, 1H); 7.41 (d, 1H), 6.77-7.34 (m, 6H); 3.61 (t, 2H); 2.95 (s, 3H); 2.89 (dd, 2H) | A | 1.56; 307.1 |
| 8 | 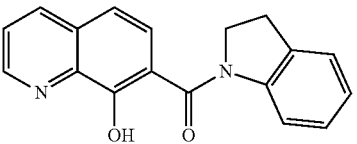 [SMILES: O=C(c1ccc2cccnc2c1O)N1CCc2ccccc21]<br>(8-Hydroxyquinolin-7-yl)(indolin-1-yl)methanone | (353K) δ: 8.93 (dd, 1H); 8.38 (dd, 1H); 7.81 (br. s, 1H); 7.63 (dd, 1H); 7.52 (d, 1H); 7.48 (d, 1H); 7.19-7.33 (m, 1H); 7.09-7.20 (m, 1H); 7.03 (td, 1H); 4.01 (t, 2H), 3.11 (t, 2H) | A | 1.56; 291.1 |

TABLE 3-continued

| Ex. | Chemical name | $^1$H-NMR (DMSO-$d_6$) | LC-MS method | $R_t$; [MH$^+$] |
|---|---|---|---|---|
| 9 | 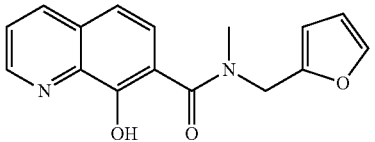 [SMILES: CN(Cc1ccco1)C(=O)c1ccc2cccnc2c1O]<br>N-(Furan-2-ylmethyl)-8-hydroxy-N-methylquinoline-7-carboxamide | (353K) δ: 8.90 (dd, 1H); 8.35 (dd, 1H); 7.61 (dd, 1H); 7.55 (dd, 1H); 7.46 (d, 1H); 7.37 (d, 1H); 6.41 (dd, 1H); 6.33 (d, 1H); 4.61 (s, 2H); 2.94 (s, 3H) | A | 1.28; 283.1 |

Example 10

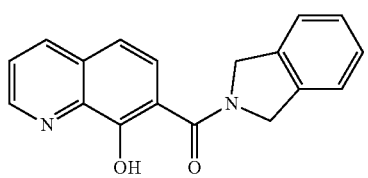 [SMILES: O=C(c1ccc2cccnc2c1O)N1Cc2ccccc2C1]

(8-Hydroxyquinolin-7-yl)(isoindolin-2-yl)methanone

A mixture of 8-hydroxyquinoline-7-carboxylic acid (189 mg, 1.0 mmol) and di(1H-imidazol-1-yl)methanone (162.2 mg, 1.0 mmol) in THF (10 mL) was heated to reflux for 4 h, under nitrogen. The reaction mixture was allowed to cool to RT and isoindoline (95.3 mg, 0.80 mmol) was added. The resulting mixture was stirred at RT for 3 h and then left to stand at RT overnight. The reaction mixture was then quenched with H$_2$O and an aqueous saturated solution of sodium hydrogen carbonate, and twice extracted with DCM. The separated organics were dried over Na$_2$SO$_4$, filtered and concentrated under reduced pressure. The residue was purified by SPE-SI cartridge (2 g, DCM to DCM:MeOH 99:1) affording the title compound (123 mg, 0.42 mmol) as a light brown solid.

LC-MS m/z (ESI$^+$): 291.2 (MH$^+$), R$_t$=3.47 min (Method C)

$^1$H-NMR (DMSO-$d_6$) δ: 8.98 (dd, 1H); 8.54 (dd, 1H); 7.74 (dd, 1H); 7.58 (m, 1H); 7.53 (m, 1H); 7.38-7.47 (m, 1H); 7.17-7.37 (m, 3H); 4.90 (s, 2H); 4.69 (s, 2H).

Following procedures analogous to the one described above, the additional compounds of the present invention were prepared (Table 4).

TABLE 4

| Ex. | Chemical name | $^1$H-NMR (DMSO-$d_6$) | LC-MS method | $R_t$; [MH$^+$] |
|---|---|---|---|---|
| 11 | 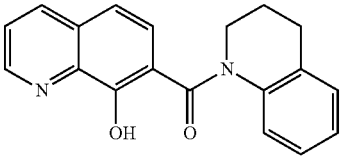 [SMILES: O=C(c1ccc2cccnc2c1O)N1CCCc2ccccc21]<br>(3,4-Dihydroquinolin-1(2H)-yl)(8-hydroxyquinolin-7-yl)methanone | δ: 8.86 (dd, 1H); 8.34 (dd, 1H); 7.60 (dd, 1H); 7.42 (s, 2H), 7.06-7.34 (m, 2H); 6.74-7.05 (m, 2H); 3.74 (t, 2H); 2.82 (t, 2H); 1.81-2.09 (m, 2H) | A | 1.55; 305.2 |
| 12 | 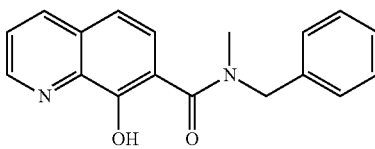<br>N-(4-Bromobenzyl)-8-hydroxy-N-methylquinoline-7-carboxamide | (353K) δ: 8.90 (dd, 1H); 8.34 (dd, 1H); 7.60 (dd, 1H); 7.53 (m, 2H); 7.36-7.49 (m, 2H); 7.31 (m, 2H); 4.62 (s, 2H); 2.89 (s, 3H) | A | 1.86; 370.95 |
| 13 | 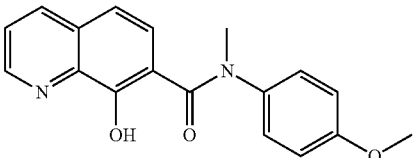<br>Hydroxy-N-(4-methoxyphenyl)-N-methylquinoline-7-carboxamide | (353K) δ: 8.81 (dd, 1H); 8.22 (dd, 1H); 7.52 (dd, 1H); 7.23-7.33 (m, 2H); 7.19 (m, 2H); 6.74 (m, 2H); 3.65 (s, 3H); 3.34 (s, 3H) | A | 1.38; 309.1 |

TABLE 4-continued

| Ex. | Chemical name | ¹H-NMR (DMSO-d₆) | LC-MS method | R_t; [MH⁺] |
|---|---|---|---|---|
| 14 | (6,7-Dimethoxy-3,4-dihydroisoquinolin-2(1H)-yl)(8-hydroxyquinolin-7-yl)methanone | (353K) δ: 8.91 (dd, 1H); 8.36 (dd, 1H); 7.61 (dd, 1H); 7.47 (d, 1H); 7.39 (d, 1H); 6.75 (s, 2H); 4.63 (s, 2H); 3.75 (s, 3H); 3.72 (s, 3H); 3.63-3.71 (m, 2H); 2.75-2.83 (m, 2H) | A | 1.42; 365.1 |
| 15 | 8-Hydroxy-N-methyl-N-phenylquinoline-7-carboxamide | δ: 10.04 (br. s, 1H); 8.65-8.95 (m, 1H); 8.06-8.35 (m, 1H); 7.44-7.72 (m, 1H); 7.02-7.35 (m, 7H); 3.37 (t, 3H) | A | 1.34; 279.1 |
| 16 | N-(4-Chlorophenyl)-8-hydroxy-N-methylquinoline-7-carboxamide | δ: 10.09 (br. s, 1H); 8.83 (dd, 1H); 8.18-8.38 (m, 1H); 7.55 (dd, 1H); 7.14-7.42 (m, 6H); 3.36 (s, 3H) | A | 1.61; 313.1 |
| 17 | N-Ethyl-8-hydroxy-N-phenylquinoline-7-carboxamide | δ: 10.01 (br. s, 1H); 8.80 (d, 1H); 8.22 (d, 1H); 7.52 (dd, 1H); 7.02-7.35 (m, 7H); 3.72-3.99 (m, 2H); 1.12 (t, 3H) | A | 1.52; 293.2 |
| 18 | N-Cyclohexyl-8-hydroxy-N-methylquinoline-7-carboxamide | (353K) δ: 8.89 (dd, 1H); 8.34 (dd, 1H); 7.59 (dd, 1H); 7.45 (d, 1H); 7.32 (d, 1H); 3.88 (br. s, 1H); 2.85 (s, 3H); 1.42-1.90 (m, 8H); 0.76-1.37 (m, 2H) | A | 1.57; 285.2 |
| 19 | 8-Hydroxy-N-methyl-N-(1-methylpiperidin-4-yl)quinoline-7-carboxamide | (353K) δ: 8.90 (dd, 1H); 8.35 (dd, 1H); 7.60 (dd, 1H); 7.46 (d, 1H); 7.33 (d, 1H); 3.86 (br. s, 1H); 2.86 (s, 3H); 2.75-2.84 (m, 2H); 2.14 (s, 3H); 1.73-2.06 (m, 4H); 1.49-1.73 (m, 2H) | A | 0.85; 300.2 |

TABLE 4-continued

| Ex. | Chemical name | ¹H-NMR (DMSO-d₆) | LC-MS method | R_t; [MH⁺] |
|---|---|---|---|---|
| 20 | 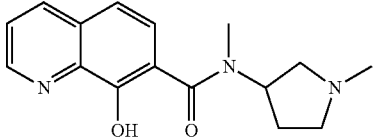 [SMILES: CN1CCC(N(C)C(=O)c2ccc3cccnc3c2O)C1]<br>8-Hydroxy-N-methyl-N-(1-methylpyrrolidin-3-yl)quinoline-7-carboxamide | δ: 8.90 (dd, 1H); 8.34 (dd, 1H); 7.60 (dd, 1H); 7.45 (d, 1H); 7.32 (d, 1H); 4.63 (br. s, 1H); 2.95 (s, 3H); 2.61-2.81 (m, 2H); 2.46 (dd, 1H); 2.24 (s, 3H); 2.14-2.24 (m, 1H); 1.94-2.13 (m, 1H): 1.69-1.96 (m, 1H) | A | 0.81; 286.2 |
| 21 | 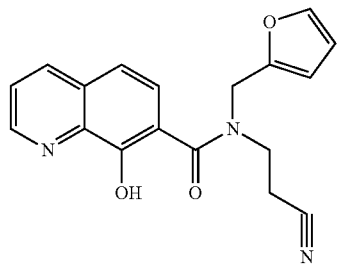 [SMILES: N#CCCN(Cc1ccco1)C(=O)c1ccc2cccnc2c1O]<br>N-(2-Cyanoethyl)-N-(furan-2-ylmethyl)-8-hydroxyquinoline-7-carboxamide | (353K) δ: 8.91 (dd, 1H); 8.35 (dd, 1H); 7.61 (dd, 1H); 7.55 (d, 1H); 7.46 (d, 1H); 7.38 (d, 1H); 6.40 (dd, 1H); 6.34 (br. s, 1H); 4.66 (s, 2H); 3.66 (t, 2H); 2.73 (t, 2H) | A | 1.30; 322.1 |
| 22 | 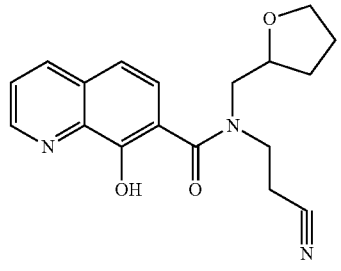 [SMILES: N#CCCN(CC1CCCO1)C(=O)c1ccc2cccnc2c1O]<br>N-(2-Cyanoethyl)-8-hydroxy-N-((tetrahydrofuran-2-yl)methyl)quinoline-7-carboxamide | δ: 8.91 (dd, 1H); 8.35 (dd, 1H); 7.61 (dd, 1H); 7.48 (d, 1H); 7.37 (d, 1H); 3.94-4.18 (m, 1H); 3.52-3.84 (m, 5H); 3.29-3.48 (m, 1H); 2.81 (t, 2H); 1.64-1.96 (m, 3H); 1.44 (br. s, 1H) | A | 1.50; 326.0 |
| 23 | 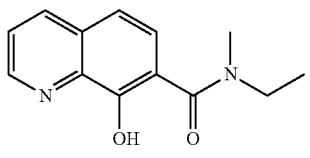 [SMILES: CCN(C)C(=O)c1ccc2cccnc2c1O]<br>N-Ethyl-8-hydroxy-N-methylquinoline-7-carboxamide | (353K) δ: 8.90 (dd, 1H); 8.34 (dd, 1H); 7.60 (dd, 1H); 7.45 (d, 1H); 7.34 (d, 1H); 3.40 (q, 2H); 2.95 (s, 3H); 1.13 (t, 3H) | A | 0.96; 231.1 |
| 24 | 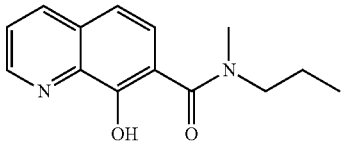 [SMILES: CCCN(C)C(=O)c1ccc2cccnc2c1O]<br>8-Hydroxy-N-methyl-N-propylquinoline-7-carboxamide | (353K) δ: 9.59 (br. s, 1H); 8.90 (dd, 1H); 8.34 (dd, 1H); 7.60 (dd, 1H); 7.45 (d, 1H); 7.34 (d, 1H); 3.35 (t, 2H); 2.95 (s, 3H); 1.60 (sxt, 2H); 0.85 (t, 3H) | A | 1.18; 245.1 |

TABLE 4-continued

| Ex. | Chemical name | ¹H-NMR (DMSO-d₆) | LC-MS method | R_t; [MH⁺] |
|---|---|---|---|---|
| 25 | (3,4-Dihydroisoquinolin-2(1H)-yl)(8-hydroxyquinolin-7-yl)methanone | (353K) δ: 8.92 (dd, 1H); 8.36 (dd, 1H); 7.62 (dd, 1H); 7.48 (d, 1H); 7.40 (d, 1H); 7.04-7.23 (m, 4H); 4.72 (s, 2H); 3.71 (t, 2H); 2.89 (t, 2H) | A | 1.48; 305.2 |
| 26 | (5-Bromoindolin-1-yl)(8-hydroxyquinolin-7-yl)methanone | δ: 10.50 (br. s, 1H); 8.94 (dd, 1H); 8.41 (dd, 1H); 8.12 (br. s, 1H); 7.66 (dd, 1H); 7.53 (d, 1H); 7.49 (d, 1H); 7.44-7.49 (m, 1H); 7.42 (br. s, 1H); 3.83-4.16 (m, 2H); 3.11 (t, 2H) | A | 1.83; 370.8 |
| 27 | (8-Hydroxyquinolin-7-yl)(6-methoxy-3,4-dihydroquinolin-1(2H)-yl)methanone hydrochloride | δ: 8.87 (dd, 1H); 8.34 (dd, 1H); 7.59 (dd, 1H); 7.43 (d, 1H); 7.39 (d, 1H); 7.17 (d, 1H); 6.74 (d, 1H); 6.47 (dd, 1H); 3.70-3.81 (m, 2H); 3.68 (s, 3H); 2.82 (t, 2H); 1.88-2.08 (m, 2H) | A | 1.57; 335.2 |
| 28 | (8-Hydroxyquinolin-7-yl)(5-nitroindolin-1-yl)methanone | δ: 10.66 (s, 1H); 8.95 (dd, 1H); 8.43 (dd, 1H); 8.16 (s, 3H); 7.67 (dd, 1H); 7.55 (d, 1H); 7.52 (d, 1H); 4.09 (t, 2H); 3.21 (t, 2H) | A | 1.68; 336.1 |
| 29 | N-(4-Bromophenyl)-8-hydroxy-N-methylquinoline-7-carboxamide | δ: 10.11 (br. s, 1H); 8.83 (dd, 1H); 8.27 (dd, 1H); 7.56 (dd, 1H); 7.26-7.47 (m, 4H); 7.21 (m, 2H); 3.36 (s, 3H) | A | 1.65; 359.0 |
| 30 | 8-Hydroxy-N-phenyl-N-propylquinoline-7-carboxamide | (353K) δ: 8.80 (dd, 1H); 8.21 (dd, 1H); 7.51 (dd, 1H); 7.28 (d, 1H); 7.24 (d, 1H); 7.21-7.28 (m, 2H); 7.13-7.21 (m, 2H); 7.04-7.11 (m, 1H); 3.71-3.94 (m, 2H); 1.59 (sxt, 2H); 0.92 (t, 3H) | A | 1.72; 307.2 |

TABLE 4-continued

| Ex. | Chemical name | ¹H-NMR (DMSO-d₆) | LC-MS method | R_t; [MH⁺] |
|---|---|---|---|---|
| 31 | 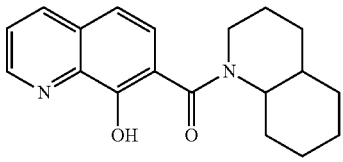 [SMILES: O=C(c1ccc2cccnc2c1O)N1CCCC2CCCCC21]<br>(8-Hydroxyquinolin-7-yl)(octahydroquinolin-1(2H)-yl)methanone | (353K) δ: 8.89 (dd, 1H); 8.34 (dd, 1H); 7.59 (dd, 1H); 7.45 (d, 1H); 7.32 (d, 1H); 4.03-4.48 (m, 1H); 3.56-3.99 (m, 1H); 2.98 (t, 1H); 1.63-2.03 (m, 5H); 0.93-1.63 (m, 8H) | A | 1.73; 311.3 |
| 32 | 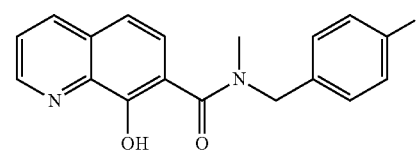<br>N-(4-Fluorobenzyl)-8-hydroxy-N-methylquinoline-7-carboxamide | (353K) δ: 8.90 (dd, 1H); 8.35 (dd, 1H); 7.60 (dd, 1H); 7.47 (d, 1H); 7.41 (d, 1H); 7.39 (m, 2H); 7.02-7.24 (m, 2H); 4.64 (s, 2H); 2.89 (s, 3H) | A | 1.57; 311.2 |
| 33 | 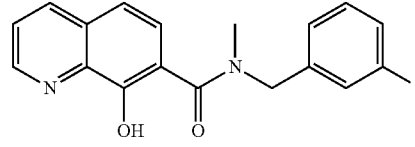<br>N-(3-Bromobenzyl)-8-hydroxy-N-methylquinoline-7-carboxamide | (353K) δ: 8.91 (dd, 1H); 8.35 (dd, 1H); 7.61 (dd, 1H); 7.53 (br. s, 1H); 7.47 (d, 1H); 7.47 (dt, 1H); 7.40 (d, 1H); 7.34-7.40 (m, 1H); 7.32 (t, 1H); 4.66 (s, 2H); 2.91 (s, 3H) | A | 1.77; 371.1 |
| 34 | 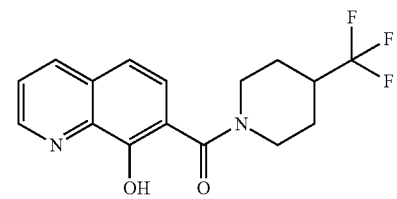 [SMILES: O=C(c1ccc2cccnc2c1O)N1CCC(C(F)(F)F)CC1]<br>(8-Hydroxyquinolin-7-yl)(4-(trifluoromethyl)piperidin-1-yl)methanone | (353K) δ: 8.90 (dd, 1H); 8.34 (dd, 1H); 7.60 (dd, 1H); 7.46 (d, 1H); 7.38 (d, 1H); 4.03-4.24 (m, 2H); 2.93-3.08 (m, 2H); 2.54-2.69 (m, 1H); 1.88 (d, 2H); 1.52 (m, 2H) | A | 1.51; 325.2 |
| 35 | 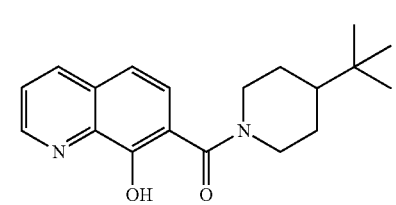 [SMILES: CC(C)(C)C1CCN(C(=O)c2ccc3cccnc3c2O)CC1]<br>(4-tert-butylpiperidin-1-yl)(8-hydroxyquinolin-7-yl)methanone | (353K) δ: 8.89 (dd, 1H); 8.33 (dd, 1H); 7.59 (dd, 1H); 7.44 (d, 1H); 7.35 (d, 1H); 4.07-4.19 (m, 2H); 2.77-2.92 (m, 2H); 1.55-1.82 (m, 2H); 1.12-1.39 (m, 3H); 0.88 (s, 9H) | A | 1.89; 313.3 |
| 36 | 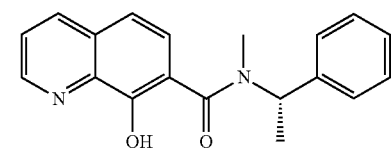 [SMILES: C[C@@H](c1ccccc1)N(C)C(=O)c1ccc2cccnc2c1O]<br>(S)-8-Hydroxy-N-methyl-N-(1-phenylethyl)quinoline-7-carboxamide | (353K) δ: 8.90 (dd, 1H); 8.35 (dd, 1H); 7.60 (dd, 1H); 7.48 (d, 1H); 7.22-7.44 (m, 6H); 5.54 (br. s, 1H); 2.68 (s, 3H); 1.60 (d, 3H) | A | 1.64; 307.2 |

TABLE 4-continued

| Ex. | Chemical name | ¹H-NMR (DMSO-d₆) | LC-MS method | R_t; [MH⁺] |
|---|---|---|---|---|
| 37 | N-Benzyl-8-hydroxy-N-(2-hydroxyethyl)quinoline-7-carboxamide | (353K) δ: 8.90 (dd, 1H); 8.34 (dd, 1H); 7.60 (dd, 1H); 7.46 (d, 1H): 7.41 (d, 1H); 7.13-7.38 (m, 5H); 4.73 (s, 2H); 3.51 (t, 2H); 3.37 (t, 2H) | A | 1.33; 323.2 |
| 38 | (3,3-Dimethylpiperidin-1-yl)(8-hydroxyquinolin-7-yl)methanone | (353K) δ: 8.89 (dd, 1H); 8.34 (dd, 1H); 7.60 (dd, 1H); 7.45 (d, 1H); 7.35 (d, 1H); 3.32-3.49 (m, 2H); 3.24 (s, 2H); 1.50-1.68 (m, 2H); 1.36-1.50 (m, 2H) 0.92 (s, 6H) | A | 1.54; 285.3 |
| 39 | N-(2-Bromobenzyl)-8-hydroxy-N-methylquinoline-7-carboxamide | (353K) δ: 8.91 (dd, 1H); 8.34 (dd, 1H); 7.59-7.66 (m, 1H); 7.61 (dd, 1H); 7.48-7.55 (m, 1H); 7.46 (d, 1H); 7.42 (d, 1H); 7.38-7.46 (m, 1H); 7.24 (td, 1H); 4.74 (s, 2H); 2.95 (s, 3H) | A | 1.84; 371.2 |
| 40 | (8-Hydroxyquinolin-7-yl)(4-phenylpiperidin-1-yl)methanone | (353K) δ: 8.90 (dd, 1H); 8.35 (dd, 1H); 7.60 (dd, 1H); 7.47 (d, 1H); 7.41 (d, 1H); 7.24-7.36 (m, 4H); 7.14-7.24 (m, 1H); 4.13-4.26 (m, 2H); 3.01-3.13 (m, 2H); 2.85 (tt, 1H); 1.78-1.97 (m, 2H); 1.53-1.78 (m, 2H) | A | 1.85; 333.3 |
| 41 | ((4aS,8S,8aR)-8-Hydroxy-octahydroquinolin-1(2H)-yl)(8-hydroxyquinolin-7-yl)methanone | δ: 10.03 (br. s, 1H); 8.90 (dd, 1H); 8.36 (dd, 1H); 7.61 (dd, 1H); 7.45 (d, 1H); 7.34 (d, 1H); 4.60-4.90 (m, 1H); 4.07-4.57 (m, 1H); 3.72-3.90 (m, 1H); 3.41-3.67 (m, 1H); 2.09-2.24 (m, 1H); 0.70-1.95 (m, 10H) | A | 1.46; 327.3 |
| 42 | (8-Hydroxyquinolin-7-yl)(2-methylpiperidin-1-yl)methanone | (353K) δ: 8.89 (dd, 1H); 8.33 (dd, 1H); 7.59 (dd, 1H); 7.45 (d, 1H); 7.33 (d, 1H); 4.29-4.58 (m, 1H); 3.80-3.93 (m, 1H); 3.03 (td, 1H); 1.33-1.80 (m, 6H); 1.22 (d, 3H) | A | 1.43; 271.2 |

TABLE 4-continued

| Ex. | Chemical name | ¹H-NMR (DMSO-d₆) | LC-MS method | $R_t$; [MH⁺] |
|---|---|---|---|---|
| 43 | (8-Hydroxyquinolin-7-yl)(2-phenylpiperidin-1-yl)methanone | (353K) δ: 8.90 (dd, 1H); 8.34 (dd, 1H); 7.60 (dd, 1H); 7.46 (d, 1H); 7.35-7.44 (m, 5H); 7.15-7.32 (m, 1H); 5.60-5.67 (m, 1H); 3.67-4.02 (m, 1H); 2.89-3.05 (m, 1H); 2.32-2.47 (m, 1H); 1.91-2.11 (m, 1H); 1.39-1.72 (m, 4H) | A | 1.98; 333.3 |
| 44 | (1,1-Dioxo-thiomorpholin-4-yl)-(8-hydroxy-quinolin-7-yl)-methanone | δ: 10.48 (br. s, 1H); 8.93 (dd, 1H); 8.39 (dd, 1H); 7.64 (dd, 1H); 7.50 (d, 1H); 7.47 (d, 1H); 4.11 (br. s, 2H); 3.68 (br. s, 2H); 3.22 (br. s, 4H) | A | 1.24; 307.2 |
| 45 | (8-Hydroxyquinolin-7-yl)-(4-methylpiperidin-1-yl)methanone | (353K) δ: 8.89 (dd, 1H); 8.34 (dd, 1H); 7.60 (dd, 1H); 7.45 (d, 1H); 7.35 (d, 1H); 4.00 (d, 2H); 2.95 (ddd, 2H); 1.51-1.82 (m, 3H); 1.05-1.26 (m, 2H); 0.96 (d, 3H) | A | 1.45; 271.2 |
| 46 | (R)-8-Hydroxy-N-(1-phenylethyl)quinoline-7-carboxamide | (353K) δ: 8.90 (dd, 1H); 8.34 (dd, 1H); 7.60 (dd, 1H); 7.48 (d, 1H); 7.41 (d, 1H); 7.33-7.42 (m, 5H); 7.22-7.32 (m, 1H); 5.55 (br. s, 1H); 2.68 (s, 3H); 1.60 (d, 3H) | A | 1.73; 307.3 |
| 47 | (8-Hydroxyquinolin-7-yl)(2-methylpyrrolidin-1-yl)methanone | (353K) δ: 8.89 (dd, 1H); 8.34 (dd, 1H); 7.60 (dd, 1H); 7.42 (q, 2H); 4.03-4.28 (m, 1H); 3.30-3.58 (m, 2H); 2.09 (dq, 1H); 1.74-2.01 (m, 2H); 1.60 (dddd, 1H); 1.16 (d, 3H) | A | 1.21; 257.2 |
| 48 | (2,5-Dimethylpyrrolidin-1-yl)(8-hydroxyquinolin-7-yl)methanone | (353K) δ: 8.89 (dd, 1H); 8.34 (dd, 1H); 7.59 (dd, 1H); 7.46 (d, 1H); 7.35 (d, 1H); 3.94-4.25 (m, 2H); 1.94-2.25 (m, 2H); 1.48-1.78 (m, 2H); 1.16 (d, 6H) | A | 1.39; 271.2 |

TABLE 4-continued

| Ex. | Chemical name | ¹H-NMR (DMSO-d₆) | LC-MS method | R_t; [MH⁺] |
|---|---|---|---|---|
| 49 | (Decahydro-1H-carbazol-9(9aH)-yl)(8-hydroxyquinolin-7-yl)methanone | δ: 10.05 (br. s, 1H); 8.90 (dd, 1H); 8.36 (dd, 1H); 7.60 (dd, 1H); 7.44 (d, 1H); 7.32 (d, 1H); 3.06-3.25 (m, 2H); 0.51-2.16 (m, 18H) | A | 2.30 351.2 |
| 50 | (8-Hydroxyquinolin-7-yl)(3-phenylpyrrolidin-1-yl)methanone | (353K) δ: 8.90 (dd, 1H); 8.34 (dd, 1H); 7.60 (dd, 1H); 7.45 (s, 2H); 7.14-7.38 (m, 5H); 3.60-4.03 (m, 1H); 3.63-3.77 (m, 1H); 3.53-3.66 (m, 1H); 3.34-3.55 (m, 2H); 2.20-2.42 (m, 1H); 1.93-2.18 (m, 1H) | A | 1.83; 319.2 |
| 51 | (3-(Dimethylamino)pyrrolidin-1-yl)(8-hydroxyquinolin-7-yl)methanone | (353K) δ: 8.90 (dd, 1H); 8.34 (dd, 1H); 7.60 (dd, 1H); 7.45 (d, 1H); 7.41 (d, 1H); 3.54-3.77 (m, 2H); 3.38-3.52 (m, 1H); 3.29 (dd, 1H); 2.75-2.91 (m, 1H); 2.17 (s, 6H); 1.97-2.12 (m, 1H); 1.79 (m, 1H) | B | 0.75; 286.3 |
| 52 | (8-Hydroxyquinolin-7-yl)(3-methylpiperidin-1-yl)methanone | (353K) δ: 8.89 (dd, 1H); 8.34 (dd, 1H); 7.60 (dd, 1H); 7.45 (d, 1H); 7.35 (d, 1H); 3.70-4.04 (m, 2H); 2.98 (ddd, 1H); 2.69 (dd, 1H); 1.75-1.88 (m, 1H); 1.59-1.75 (m, 2H); 1.40-1.59 (m, 1H); 1.09-1.27 (m, 1H); 0.86 (d, 3H) | A | 1.40; 271.2 |
| 53 | (8-Hydroxyquinolin-7-yl)(pyrrolidin-1-yl)methanone | (353K) δ: 8.90 (dd, 1H); 8.33 (dd, 1H); 7.60 (dd, 1H); 7.45 (d, 1H); 7.41 (d, 1H); 3.34-3.64 (m, 4H); 1.71-2.04 (m, 4H) | A | 1.01; 243.2 |
| 54 | (1,4-Dioxa-8-aza-spiro[4.5]dec-8-yl)-(8-hydroxy-quinolin-7-yl)-methanone | (353K) δ: 8.90 (dd, 1H); 8.34 (dd, 1H); 7.60 (dd, 1H); 7.46 (d, 1H); 7.38 (d, 1H); 3.93 (s, 4H); 3.49-3.68 (m, 4H); 1.63-1.79 (m, 4H) | A | 1.08; 315.2 |

TABLE 4-continued

| Ex. | Chemical name | ¹H-NMR (DMSO-d₆) | LC-MS method | R$_t$; [MH⁺] |
|---|---|---|---|---|
| 55 | 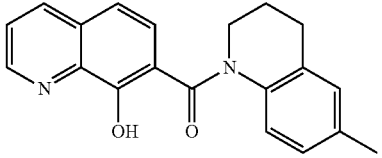 [SMILES: Cc1ccc2c(c1)CCCN2C(=O)c1ccc2cccnc2c1O]<br>(8-Hydroxyquinolin-7-yl)(6-methyl-3,4-dihydroquinolin-1(2H)-yl)methanone | (353K) δ: 8.86 (dd, 1H); 8.31 (dd, 1H); 7.58 (dd, 1H); 7.41 (d, 1H); 7.39 (d, 1H); 7.13 (d, 1H); 6.90-7.02 (m, 1H); 6.58-6.78 (m, 1H); 3.67-3.86 (m, 2H); 2.75-2.85 (m, 2H); 2.19 (s, 3H); 1.99 (m, 2H) | A | 1.81; 327.2 |
| 56 | 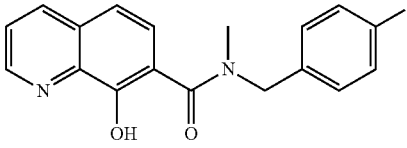<br>N-(4-Chlorobenzyl)-8-hydroxy-N-methylquinoline-7-carboxamide | (353K) δ: 8.90 (dd, 1H); 8.35 (dd, 1H); 7.60 (dd, 1H); 7.47 (d, 1H); 7.41 (d, 1H); 7.33-7.42 (m, 4H); 4.65 (s, 2H); 2.90 (s, 3H) | A | 1.81; 319.2 |
| 57 | 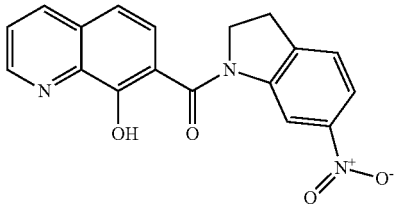 [SMILES: O=C(c1ccc2cccnc2c1O)N1CCc2ccc([N+](=O)[O-])cc21]<br>(8-Hydroxyquinolin-7-yl)(6-nitroindolin-1-yl)methanone | δ: 10.61 (br. s, 1H); 8.88-9.01 (m, 2H); 8.43 (dd, 1H); 778-8.08 (m, 1H); 7.68 (m, 1H); 7.47-7.60 (m, 3H); 3.95-4.22 (m, 2H); 3.16-3.28 (m, 2H) | A | 1.65; 336.1 |
| 58 | 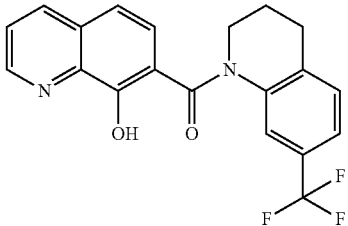 [SMILES: O=C(c1ccc2cccnc2c1O)N1CCCc2ccc(C(F)(F)F)cc21]<br>(8-Hydroxyquinolin-7-yl)(7-(trifluoromethyl)-3,4-dihydroquinolin-1(2H)-yl)methanone | δ: 10.25 (br. s, 1H); 8.87 (dd, 1H); 8.36 (dd, 1H); 7.61 (dd, 1H); 7.65 (br. s, 1H); 7.43-7.53 (m, 2H); 7.36-7.43 (m, 1H); 7.24-7.34 (m, 1H); 3.77 (t, 2H); 2.90 (t, 2H); 1.98 (quin, 2H) | A | 2.03; 373.1 |
| 59 | 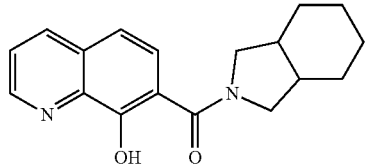 [SMILES: O=C(c1ccc2cccnc2c1O)N1CC2CCCCC2C1]<br>(Hexahydro-1H-isoindol-2(3H)-yl)(8-hydroxyquinolin-7-yl)methanone | δ: 10.28 (br. s, 1H); 8.91 (dd, 1H); 8.36 (dd, 1H); 7.62 (dd, 1H); 7.45 (d, 1H); 7.39 (d, 1H); 3.32-3.57 (m, 3H); 3.07-3.22 (m, 1H); 2.06-2.32 (m, 2H); 1.27-1.60 (m, 8H) | A | 1.62; 297.3 |

Example 60

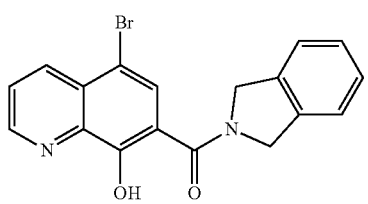 [SMILES: O=C(c1cc(Br)c2cccnc2c1O)N1Cc2ccccc2C1]

(5-Bromo-8-hydroxyquinolin-7-yl)(isoindolin-2-yl)methanone

A mixture of 5-bromo-8-hydroxyquinoline-7-carboxylic acid of Preparation 4 (150 mg, 0.56 mmol) and di(1H-imidazol-1-yl)methanone (90.7 mg, 0.56 mmol) in THF (10 mL) was heated to reflux for 3 h, under nitrogen. The reaction mixture was allowed to cool to RT and isoindoline (53 mg, 0.45 mmol) was added. The resulting mixture was stirred at RT overnight. The reaction mixture was then quenched with $H_2O$ and an aqueous saturated solution of sodium hydrogen carbonate, and twice extracted with DCM. The separated organics were dried over $Na_2SO_4$, filtered and concentrated under reduced pressure. The residue was purified by SPE-SI cartridge (2 g, DCM to DCM:MeOH 99:1) affording the title compound (39.1 mg, 0.11 mmol) as a light brown solid.

LC-MS m/z (ESI$^+$): 369.09 (MH$^+$), $R_t$=2.21 min (Method A)

$^1$H-NMR (DMSO-d$_6$) δ: 10.80 (br. s, 1H); 8.96-9.07 (m, 1H); 8.45-8.54 (m, 1H); 7.76-7.87 (m, 2H); 7.42 (d, 1H); 7.18-7.37 (m, 3H); 4.88 (s, 2H); 4.71 (s, 2H).

Example 61

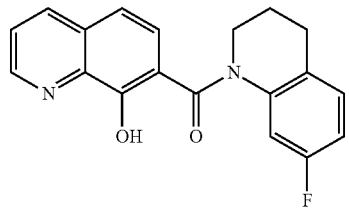 [SMILES: O=C(c1ccc2cccnc2c1O)N1CCCc2ccc(F)cc21]

(7-Fluoro-3,4-dihydroquinolin-1(2H)-yl)(8-hydroxyquinolin-7-yl)methanone

A mixture of 8-hydroxyquinoline-7-carboxylic acid (100 mg, 0.53 mmol) and di(1H-imidazol-1-yl)methanone (86 mg, 0.53 mmol) in THF (6 mL) was heated to reflux for 4 h, under nitrogen. The reaction mixture was allowed to cool to RT and 7-fluoro-1,2,3,4-tetrahydroquinoline hydrochloride (84.4 mg, 0.45 mmol) and TEA (0.062 mL, 0.45 mmol) were added. The resulting mixture was heated in a MW oven at 120° C. for 90 min and then at 140° C. for 2 h. The reaction mixture was then quenched with $H_2O$ and an aqueous saturated solution of sodium hydrogen carbonate, and twice extracted with DCM. The separated organics were dried over $Na_2SO_4$, filtered and concentrated under reduced pressure. The residue was purified by preparative HPLC. Product-containing fractions were combined, made basic with a saturated aqueous solution of sodium hydrogen carbonate and $CH_3CN$ was removed under reduced pressure. The aqueous phase was extracted with DCM and the separated organics dried over $Na_2SO_4$, filtered and concentrated to dryness, affording the title compound (19 mg, 0.06 mmol) as a off-white solid.

LC-MS m/z (ESI$^+$): 323.1 (MH$^+$), $R_t$=1.78 min (Method A)

$^1$H-NMR (DMSO-d$_6$) δ: 8.88 (dd, 1H); 8.36 (dd, 1H); 7.61 (dd, 1H); 7.47 (d, 1H); 7.43 (d, 1H); 7.25-7.36 (m, 1H); 7.20 (dd, 1H); 6.85 (td, 1H); 3.62-3.78 (m, 2H); 2.80 (t, 2H); 1.93 (m, 2H).

Following procedures analogous to the one described above, the additional compounds of the present invention were prepared (Table 5).

TABLE 5

| Ex. | Chemical name | $^1$H NMR (DMSO-d$_6$) | LC-MS method | $R_t$; [MH$^+$] |
|---|---|---|---|---|
| 62 | (8-Hydroxyquinolin-7-yl)(2-methyl-3,4-dihydroquinolin-1(2H)-yl)methanone | δ: 10.00 (br. s, 1H); 8.84 (dd, 1H); 8.31 (dd, 1H); 7.57 (dd, 1H); 7.36 (s, 2H); 7.16 (d, 1H); 6.89-7.04 (m, 1H); 6.86-7.06 (m, 1H); 6.81 (br. s, 1H); 4.57-4.72 (m, 1H); 2.59-2.86 (m, 2H); 2.30-2.46 (m, 1H); 1.38-1.61 (m, 1H); 1.14 (d, 3H) | A | 1.73; 319.1 |
| 63 | (8-Hydroxyquinolin-7-yl)(3-methyl-3,4-dihydroquinolin-1(2H)-yl)methanone | δ: 10.16 (br. s, 1H); 8.87 (dd, 1H); 8.35 (dd, 1H); 7.60 (dd, 1H); 7.43 (s, 2H); 7.28 (br. s, 1H); 7.06-7.22 (m, 1H); 6.77-7.06 (m, 2H); 3.81-4.01 (m, 1H); 3.25 (dd, 1H); 2.95 (dd, 1H); 2.48 (dd, 1H); 1.99-2.25 (m, 1H); 0.99 (d, 3H) | A | 1.81; 319.1 |

TABLE 5-continued

| Ex. | Chemical name | ¹H NMR (DMSO-d₆) | LC-MS method | R_t; [MH⁺] |
|---|---|---|---|---|
| 64 | 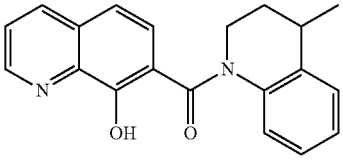 [SMILES: CC1CCN(C(=O)c2ccc3cccnc3c2O)c2ccccc21]<br>(8-Hydroxyquinolin-7-yl)(4-methyl-3,4-dihydroquinolin-1(2H)-yl)methanone | δ: 10.11 (br. s, 1H); 8.86 (dd, 1H); 8.34 (dd, 1H); 7.59 (dd, 1H); 7.42 (s, 2H), 7.07-7.34 (m, 2H); 6.92-7.07 (m, 1H); 6.71-6.92 (m, 1H); 3.59-3.87 (m, 2H); 2.85-3.08 (m, 1H); 2.01-2.24 (m, 1H); 1.60 (m, 1H); 1.33 (d, 3H) | C | 2.65; 319.1 |
| 65 | 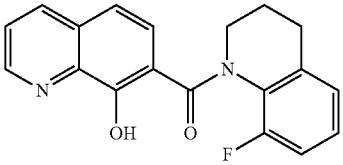 [SMILES: O=C(c1ccc2cccnc2c1O)N1CCCc2cccc(F)c21]<br>(8-Fluoro-3,4-dihydroquinolin-1(2H)-yl)(8-hydroxyquinolin-7-yl)methanone | δ: 10.15 (br. s, 1H); 8.86 (dd, 1H); 8.34 (dd, 1H); 7.60 (dd, 1H); 7.44 (d, 1H); 7.40 (d, 1H); 6.97-7.21 (m, 2H); 6.73-6.97 (m, 1H); 3.73 (br. s, 2H); 2.85 (t, 2H); 1.82-2.09 (m, 2H) | A | 1.63; 323.1 |
| 66 | 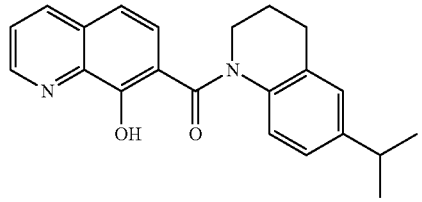 [SMILES: CC(C)c1ccc2c(c1)CCCN2C(=O)c1ccc2cccnc2c1O]<br>(8-Hydroxyquinolin-7-yl)(6-isopropyl-3,4-dihydroquinolin-1(2H)-yl)methanone | (353K) δ: 8.86 (dd, 1H); 8.31 (dd, 1H); 7.58 (dd, 1H); 7.40 (s, 2H); 7.27 (d, 1H); 7.02 (d, 1H); 6.79 (dd, 1H); 3.66-3.79 (m, 2H); 2.76-2.90 (m, 3H); 1.98 (dq, 2H); 1.16 (d, 6H) | A | 2.12; 347.1 |
| 67 | 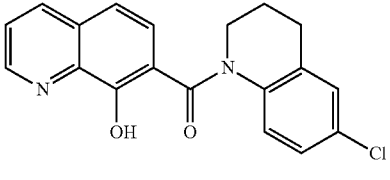 [SMILES: O=C(c1ccc2cccnc2c1O)N1CCCc2cc(Cl)ccc21]<br>(6-Chloro-3,4-dihydroquinolin-1(2H)-yl)(8-hydroxyquinolin-7-yl)methanone | δ: 10.19 (br. s, 1H); 8.87 (dd, 1H); 8.35 (dd, 1H); 7.61 (dd, 1H); 7.47 (d, 1H); 7.43 (d, 1H); 7.07-7.39 (m, 2H); 6.94 (d, 1H); 3.73 (t, 2H); 2.82 (t, 2H); 1.95 (m, 2H) | C | 2.87; 338.95 |
| 68 | 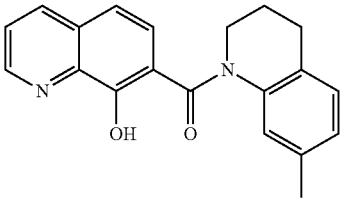 [SMILES: Cc1ccc2c(c1)N(C(=O)c1ccc3cccnc3c1O)CCC2]<br>(8-Hydroxyquinolin-7-yl)(7-methyl-3,4-dihydroquinolin-1(2H)-yl)methanone | δ: 8.86 (dd, 1H); 8.34 (dd, 1H); 7.59 (dd, 1H); 7.41 (s, 2H); 7.20 (br. s, 1H); 7.03 (d, 1H); 6.80 (d, 1H); 3.69 (t, 2H); 2.68-2.87 (m, 2H); 2.02 (br. s, 3H); 1.92 (m, 2H) | A | 1.78; 319.1 |
| 69 | 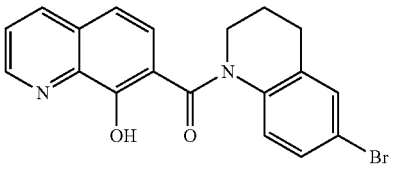 [SMILES: O=C(c1ccc2cccnc2c1O)N1CCCc2cc(Br)ccc21]<br>(6-Bromo-3,4-dihydroquinolin-1(2H)-yl)(8-hydroxyquinolin-7-yl)methanone | δ: 8.86 (dd, 1H); 8.34 (dd, 1H); 7.59 (dd, 1H); 7.32-7.51 (m, 3H); 7.13-7.32 (m, 1H); 6.88-7.13 (m, 1H); 3.73 (t, 2H); 2.82 (t, 2H); 1.85-2.06 (m, 2H) | A | 2.03; 382.96 |

TABLE 5-continued

| Ex. | Chemical name | ¹H NMR (DMSO-d$_6$) | LC-MS method | R$_t$; [MH$^+$] |
|---|---|---|---|---|
| 70 | (5,7-Difluoro-3,4-dihydroquinolin-1(2H)-yl)(8-hydroxyquinolin-7-yl)methanone | δ: 8.89 (dd, 1H); 8.37 (dd, 1H); 7.62 (dd, 1H); 7.50 (d, 1H); 7.46 (d, 1H); 7.09-7.34 (m, 1H); 6.93 (td, 1H); 3.50-3.82 (m, 2H); 2.68-2.82 (m, 2H); 1.89-2.01 (m, 2H) | A | 1.99; 341.1 |
| 71 | (5-Fluoro-3,4-dihydroquinolin-1(2H)-yl)(8-hydroxyquinolin-7-yl)methanone | δ: 10.23 (br. s, 1H); 8.87 (dd, 1H); 8.35 (dd, 1H); 7.60 (dd, 1H); 7.47 (d, 1H); 7.43 (d, 1H); 7.16 (br. s, 1H); 6.89-7.00 (m, 1H); 6.75-6.89 (m, 1H); 3.65-3.85 (m, 2H); 2.80 (t, 2H); 1.90-2.07 (m, 2H) | A | 1.82; 323.1 |
| 72 | (6-Fluoro-3,4-dihydroquinolin-1(2H)-yl)(8-hydroxyquinolin-7-yl)methanone | δ: 8.85 (dd, 1H); 8.34 (dd, 1H); 7.59 (dd, 1H); 7.44 (d, 1H); 7.23-7.43 (m, 2H); 7.02 (dd, 1H); 6.56-6.88 (m, 1H); 3.59-3.86 (m, 2H); 2.83 (t, 2H); 1.86-2.07 (m, 2H) | A | 2.60; 323.1 |
| 73 | (5-Chloro-8-hydroxy-3,4-dihydroquinolin-1(2H)-yl)(8-hydroxyquinolin-7-yl)methanone | δ: 8.82 (dd, 1H); 8.29 (dd, 1H); 7.56 (dd, 1H); 7.44 (d, 1H); 7.32 (d, 1H); 6.97 (d, 1H); 6.45 (d, 1H); 3.47-3.79 (m, 2H); 2.83 (t, 2H); 1.84-2.16 (m, 2H) | A | 1.71; 355 |
| 74 | (2H-Benzo[b][1,4]oxazin-4(3H)-yl)(3-hydroxyquinolin-7-yl)methanone | δ: 10.37 (br. s, 1H); 8.90 (dd, 1H); 8.38 (dd, 1H); 7.63 (dd, 1H); 7.54 (br. s, 1H); 7.52 (m, 1H); 7.48 (d, 1H); 6.94-7.06 (m, 1H); 6.90 (dd, 1H); 6.75 (br. s, 1H); 4.31 (t, 2H); 3.83 (br. s, 2H) | F | 1.42; 306.9 |

2. Activity Testing: Methods and Results

Organisms Used to Test Antifungal Activity

*Trichophyton Rubrum* (ATCC 28188, PBI International), *Trichophyton Mentagrophytes* (ATCC 9533, PBI International), *Aspergillus Niger* (ATCC 16404, PBI International), *Scopulariopsis Brevicaulis* (ATCC 36840, DSMZ), *Candida Albicans* (ATCC 90028, PBI International), *Candida Glabrata* (ATCC 90030, DSMZ).

Preparation and Conservation

Strains were prepared from freeze-dried ampoules or freeze-dried pellets. An isolation of the suspensions was made on Potato Dextrose Agar (PDA) to test the strains purity. A strains' massive growth was then made streaking microbial suspensions on PDA plates.

Incubation was at 30° C. for 48-72 hours (*Candida* yeasts) and for 7-10 days (filamentous fungi).

The yeasts' colonies and the filamentous fungi's conidia were harvested with 3-5 mL of RPMI 1640+50% glycerol and the aliquots frozen at −80° C.

Antifungal Susceptibility Testing

Compounds' minimal inhibition concentration (MIC) was determined through broth micro-dilution susceptibility test using a method developed in agreement with the National Committee for Clinical Laboratory Standards (NCCLS) (National Committee for Clinical Laboratory Standards. Reference Method for Broth Dilution Antifungal Susceptibility Testing of Yeasts; Approved standard-Second Edition M27-A2. 2002; Vol. 22, No. 15) (National Committee for Clinical Laboratory Standards. Reference Method for Broth Dilution Antifungal Susceptibility Testing of Filamentous Fungi; Approved standard M38-A. 2002; Vol. 22, No. 16).

Assays were carried out in RPMI 1640 with L-glutamine medium buffered to pH 7 with 0.165M 3-(N-morpholino)propanesulfonic acid (MOPS) and 10M NaOH and supplemented with 18 g glucose/litre. The tests were performed using 96 well sterile plates (inoculum size of $1\times10^5$ CFU/mL). Compounds stock solutions were prepared at 12.8 mg/mL in 100% DMSO. A series of twofold dilutions were prepared in plate using RPMI 1640. Final concentrations ranged from 0.125 to 128 μg/mL at 1% DMSO.

MIC is defined as the lowest concentration of antifungal agent which prevents any visible growth and was determined after 48 h of incubation for yeasts (35° C.) and after five days of incubation for filamentous fungi (35° C.).

RESULTS

The MIC values for the most preferable compounds, calculated as the geometric means of the values obtained in two single experiments, are reported in Table 6.

TABLE 6

| Ex | Trycophyton Rubrum ATCC 28188 | Tricophyton Mentagrophytes ATCC 9533 | Aspergillus Niger ATCC 16404 | Scopulariopsis Brevicaulis ATCC 36840 | Candida Albicans ATCC 90028 | Candida Glabrata ATCC 90030 |
|---|---|---|---|---|---|---|
| 10 | 1.00 | 2.00 | 0.25 | 2.00 | 2.00 | 2.00 |
| 6  | 1.41 | 1.41 | 0.50 | 1.41 | 1.41 | 2.00 |
| 29 | 2.00 | 1.00 | 0.13 | 2.00 | 4.00 | 4.00 |
| 49 | 0.71 | 1.41 | 0.25 | 1.00 | 2.00 | 2.83 |
| 56 | 2.00 | 1.00 | 0.71 | 2.00 | 1.41 | 2.00 |
| 70 | 1.00 | 2.00 | 0.25 | 1.00 | 2.00 | 1.00 |
| 61 | 1.00 | 2.00 | 0.25 | 0.71 | 2.00 | 2.00 |
| 71 | 1.00 | 2.00 | 0.25 | 0.71 | 2.00 | 2.83 |
| 72 | 1 | 2 | 0.25 | 0.50 | 2 | 2 |
| 73 | 2 | 2 | 0.125 | 4 | 2 | 1 |
| 74 | 1 | 1.41 | 0.18 | 0.71 | 2 | 2 |

The invention claimed is:

1. A compound selected from those of general formula (I)

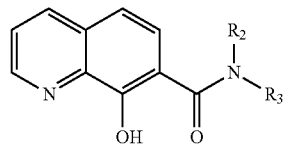

(I)

and pharmaceutically acceptable salts and derivatives thereof,
wherein
$R_2$ and $R_3$, independently from each other, are selected from:
a) —$C_1$-$C_6$ alkyl, with the proviso that $R_2$ and $R_3$ are not both methyl,
b) —$(CH_2)_n$-aryl, 4-halo-benzyl or 4-halo-phenyl,
c) —$(CH_2)_n$-cycloalkyl,
d) —$(CH_2)_n$-heterocycle,
e) —$(CH_2)_n$—$OR_6$,
f) —$(CH_2)_n$—CN,
g) —$(CH_2)_n$—$NR_4R_5$,
h) taken together with the nitrogen atom to which they are attached form a 5- to 8-membered heteromonocycle having from one to three additional heteroatoms selected from the group consisting of oxygen and sulphur, or
i) taken together with the nitrogen atom to which they are attached form: (i) a 5- to 8-membered heteromonocycle which is fused to one or two saturated or unsaturated rings or to other heterocycles having from one to three heteroatoms selected from the group consisting of nitrogen, oxygen and sulphur; or (ii) a halo and/or hydroxy substituted dihydroquinoline;

$R_4$ and $R_5$, independently from each other, are selected from:
a) —H,
b) —$C_1$-$C_6$ alkyl,
c) —$(CH_2)_n$-aryl,
d) —$(CH_2)_n$-cycloalkyl,
e) —$(CH_2)_n$-heterocycle,
f) —$(CH_2)_n$—$OR_6$,
g) —$(CH_2)_n$—CN,
h) taken together with the nitrogen atom to which they are attached form a 5- to 8-membered heteromonocycle having from one to three heteroatoms selected from the group consisting of nitrogen, oxygen and sulphur, or
j) taken together with the nitrogen atom to which they are attached form a 5- to 8-membered heteromonocycle which is fused to one or two saturated or unsaturated rings or to other heterocycles having from one to three heteroatoms selected from the group consisting of nitrogen, oxygen and sulphur;

$R_6$ is selected from:
a) —H,
b) —$C_1$-$C_6$ alkyl,
c) —$(CH_2)_n$-aryl,
d) —$(CH_2)_n$-cycloalkyl, or
e) —$(CH_2)_n$-heterocycle; and
n is an integer from 0 to 6.

2. The compound according to claim 1,
wherein $R_2$ and $R_3$, independently from each other, are selected from:
a) —$C_1$-$C_6$ alkyl, with the proviso that $R_2$ and $R_3$ are not both methyl,
b) —$(CH_2)_n$-aryl, 4-halo-benzyl or 4-halo-phenyl,
c) —$(CH_2)_n$-cycloalkyl,
d) —$(CH_2)_n$-heterocycle,
e) —$(CH_2)_n$—$OR_6$, f) —(CH$_2$)$_n$—CN,
g) taken together with the nitrogen atom to which they are attached form a 5- to 8-membered heteromonocycle having from one to three additional heteroatoms selected from the group consisting of oxygen and sulphur, or
h) taken together with the nitrogen atom to which they are attached form: (i) a 5- to 8-membered heteromonocycle which is fused to one or two a unsaturated or saturated rings or to other heterocycles having from one to three heteroatoms selected from the group consisting of nitrogen, oxygen and sulphur; or (ii) a halo and/or hydroxy substituted dihydroquinoline;

and R$_6$ is H.

3. The compound according to claim 1, wherein R$_2$ and R$_3$, independently from each other, are selected from:
a) —C$_1$-C$_6$ alkyl, with the proviso that R$_2$ and R$_3$ are not both methyl,
b) —(CH$_2$)$_n$-aryl, 4-halo-benzyl or 4-halo-phenyl or
c) taken together with the nitrogen atom to which they are attached form: (i) a 5- to 8-membered heteromonocycle which is fused to one or two a unsaturated or saturated rings or to other heterocycles having from one to three heteroatoms selected from the group consisting of nitrogen, oxygen and sulphur; or (ii) a halo and/or hydroxy substituted dihydroquinoline.

4. The compound according to claim 1, wherein R$_2$ and R$_3$ taken together with the nitrogen atom to which they are attached form a 5- to 8-membered heteromonocycle which is fused to one or two unsaturated or saturated rings or to other heterocycles containing from one to three heteroatoms selected from the group consisting of nitrogen, oxygen and sulphur.

5. The compound according to claim 1, wherein n is an integer from 0 to 2.

6. A compound selected from the group consisting of:
8-Hydroxy-N-methyl-N-(4-(2-phenylpropan-2-yl)benzyl)quinoline-2-carboxamide;
N-Benzyl-8-hydroxy-N-methylquinoline-7-carboxamide;
(8-Hydroxyquinolin-7-yl)(isoindolin-2-yl)methanone;
(8-Hydroxyquinolin-7-yl)(morpholino)methanone;
(8-Hydroxyquinolin-7-yl)(piperidin-1-yl)methanone;
8-Hydroxy-N-methyl-N-phenethylquinoline-7-carboxamide;
(8-Hydroxyquinolin-7-yl)(indolin-1-yl)methanone;
N-(Furan-2-ylmethyl)-8-hydroxy-N-methylquinoline-7-carboxamide;
(3,4-Dihydroquinolin-1(2H)-yl)(8-hydroxyquinolin-7-yl)methanone;
N-(4-Bromobenzyl)-8-hydroxy-N-methylquinoline-7-carboxamide;
8-Hydroxy-N-(4-methoxyphenyl)-N-methylquinoline-7-carboxamide;
(6,7-Dimethoxy-3,4-dihydroisoquinolin-2(1H)-yl)(8-hydroxyquinolin-7-yl)methanone;
8-Hydroxy-N-methyl-N-(tetrahydro-2H-pyran-4-yl)quinoline-7-carboxamide;
8-Hydroxy-N-methyl-N-phenylquinoline-7-carboxamide;
N-(4-Chlorophenyl)-8-hydroxy-N-methylquinoline-7-carboxamide;
N-Ethyl-8-hydroxy-N-phenylquinoline-7-carboxamide;
N-Cyclohexyl-8-hydroxy-N-methylquinoline-7-carboxamide;
8-Hydroxy-N-methyl-N-(1-methylpiperidin-4-yl)quinoline-7-carboxamide;
8-Hydroxy-N-methyl-N-(1-methylpyrrolidin-3-yl)quinoline-7-carboxamide;
N-(2-Cyanoethyl)-N-(furan-2-ylmethyl)-8-hydroxyquinoline-7-carboxamide;
N-(2-Cyanoethyl)-8-hydroxy-N-((tetrahydrofuran-2-yl)methyl)quinoline-7-carboxamide;
N-Ethyl-8-hydroxy-N-methylquinoline-7-carboxamide;
8-Hydroxy-N-methyl-N-propylquinoline-7-carboxamide;
(3,4-Dihydroisoquinolin-2(1H)-yl)(8-hydroxyquinolin-7-yl)methanone;
(5-Bromoindolin-1-yl)(8-hydroxyquinolin-7-yl)methanone;
(8-Hydroxyquinolin-7-yl)(6-methoxy-3,4-dihydroquinolin-1(2H)-yl)methanone;
(8-Hydroxyquinolin-7-yl)(5-nitroindolin-1-yOmethanone;
8-Hydroxy-N-phenyl-N-propylquinoline-7-carboxamide;
(8-Hydroxyquinolin-7-yl)(octahydroquinolin-1(2H)-yl)methanone;
N-(4-Fluorobenzyl)-8-hydroxy-N-methylquinoline-7-carboxamide;
N-(3-Bromobenzyl)-8-hydroxy-N-methylquinoline-7-carboxamide;
(8-Hydroxyquinolin-7-yl)(4-(trifluoromethyl)piperidin-1-yl)methanone;
(4-tert-Butylpiperidin-1-yl)(8-hydroxyquinolin-7-yl)methanone;
(S)-8-Hydroxy-N-methyl-N-(1-phenylethyl)quinoline-7-carboxamide;
N-Benzyl-8-hydroxy-N-(2-hydroxyethyl)quinoline-7-carboxamide;
(3,3-Dimethylpiperidin-1-yl)(8-hydroxyquinolin-7-yl)methanone;
N-(2-Bromobenzyl)-8-hydroxy-N-methylquinoline-7-carboxamide;
(8-Hydroxyquinolin-7-yl)(4-phenylpiperidin-1-yl)methanone;
((4aS,8S,8aR)-8-Hydroxy-octahydroquinolin-1(2H)-yl)(8-hydroxyquinolin-7-yl)methanone;
(8-Hydroxyquinolin-7-yl)(2-methylpiperidin-1-yl)methanone;
(8-Hydroxyquinolin-7-yl)(2-phenylpiperidin-1-yl)methanone;
(1,1-Dioxo-thiomorpholin-4-yl)-(8-hydroxy-quinolin-7-yl)-methanone;
(8-Hydroxyquinolin-7-yl)(4-methylpiperidin-1-yl)methanone;
(R)-8-Hydroxy-N-(1-phenylethyl)quinoline-7-carboxamide;
(8-Hydroxyquinolin-7-yl)(2-methylpyrrolidin-1-yl)methanone;
(2,5-Dimethylpyrrolidin-1-yl)(8-hydroxyquinolin-7-yl)methanone;
(8-Hydroxyquinolin-7-yl)(3-phenylpyrrolidin-1-yl)methanone;
(3-(Dimethylamino)pyrrolidin-1-yl)(8-hydroxyquinolin-7-yl)methanone;
(8-Hydroxyquinolin-7-yl)(3-methylpiperidin-1-yl)methanone;
(8-Hydroxyquinolin-7-yl)(pyrrolidin-1-yl)methanone;
(1,4-Dioxa-8-aza-spiro[4.5]dec-8-yl)-(8-hydroxy-quinolin-7-yl)-methanone;
(8-Hydroxyquinolin-7-yl)(6-methyl-3,4-dihydroquinolin-1(2H)-yl)methanone;
(8-Hydroxyquinolin-7-yl)(6-nitroindolin-1-yl)methanone;

(8-Hydroxyquinolin-7-yl)(7-(trifluoromethyl)-3,4-dihydroquinolin-1(2H)-yl)methanone;
(5-Bromo-8-hydroxyquinolin-7-yl)(isoindolin-2-yl)methanone;
(Hexahydro-1H-isoindol-2(3H)-yl)(8-hydroxyquinolin-7-yl)methanone;
(8-Hydroxyquinolin-7-yl)(2-methyl-3,4-dihydroquinolin-1(2H)-yl)methanone;
(8-Hydroxyquinolin-7-yl)(3-methyl-3,4-dihydroquinolin-1(2H)-yl)methanone;
(8-Hydroxyquinolin-7-yl)(4-methyl-3,4-dihydroquinolin-1(2H)-yl)methanone;
(8-Fluoro-3,4-dihydroquinolin-1(2H)-yl)(8-hydroxyquinolin-7-yl)methanone;
(8-Hydroxyquinolin-7-yl)(6-isopropyl-3,4-dihydroquinolin-1(2H)-yl)methanone;
(6-Chloro-3,4-dihydroquinolin-1(2H)-yl)(8-hydroxyquinolin-7-yl)methanone;
(8-Hydroxyquinolin-7-yl)(7-methyl-3,4-dihydroquinolin-1(2H)-yl)methanone;
(6-Bromo-3,4-dihydroquinolin-1(2H)-yl)(8-hydroxyquinolin-7-yl)methanone; (8-Hydroxyquinolin-7-yl)(octahydroisoquinolin-2(1H)-yl)methanone;
N-(4-Bromophenyl)-8-hydroxy-N-methylquinoline-7-carboxamide;
(Decahydro-1H-carbazol-9(9aH)-yl)(8-hydroxyquinolin-7-yl)methanone;
N-(4-Chlorobenzyl)-8-hydroxy-N-methylquinoline-7-carboxamide;
(5,7-Difluoro-3,4-dihydroquinolin-1(2H)-yl)(8-hydroxyquinolin-7-yl)methanone;
(7-Fluoro-3,4-dihydroquinolin-1(2H)-yl)(8-hydroxyquinolin-7-yl)methanone;
(5-Fluoro-3,4-dihydroquinolin-1(2H)-yl)(8-hydroxyquinolin-7-yl)methanone;
(6-Fluoro-3,4-dihydroquinolin-1(2H)-yl)(8-hydroxyquinolin-7-yl)methanone;
(5-Chloro-8-hydroxy-3,4-dihydroquinolin-1(2H)-yl)(8-hydroxyquinolin-7-yl)methanone;
and (2H-Benzo[b][1,4]oxazin-4(3H)-yl)(8-hydroxyquinolin-7-yl)methanone.

7. A compound of formula

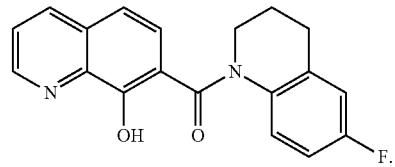 [SMILES: O=C(c1ccc2cccnc2c1O)N1CCCc2cc(F)ccc21]

8. A method of treating a fungal infection, in a subject in need thereof, comprising administration of an effective amount of the compound according to claim 1.

9. The method according to claim 8, wherein the fungal infection is from *Tricophyton Rubrum, Tricophyton Mentagrophytes, Aspergillus Niger, Scopulariopsis Brevicaulis* or *Candida*.

10. The method according to claim 9, wherein the fungal infection is from *Candida Albicans* or *Candida Glabrata*.

11. The method according to claim 8, wherein the subject is a mammal.

12. The method according to claim 11, wherein the subject is a human.

13. A pharmaceutical formulation comprising at least one compound according to claim 1, together with at least a pharmaceutically acceptable carrier, excipient and/or adjuvant.

\* \* \* \* \*

UNITED STATES PATENT AND TRADEMARK OFFICE
CERTIFICATE OF CORRECTION

PATENT NO. : 8,729,098 B2
APPLICATION NO. : 13/519206
DATED : May 20, 2014
INVENTOR(S) : Stefania Gagliardi et al.

It is certified that error appears in the above-identified patent and that said Letters Patent is hereby corrected as shown below:

On the Title Page, Item (56), Other Publications:

"Baret, P. et al, Journal of the American Chemical Society, vol. 117, No. 38, p. 9760-9761, 1996"

should be

--Baret, P. et al, Journal of the American Chemical Society, vol. 117, No. 38, p. 9760-9761, 1995--.

On the Title Page, Item (56), Other Publications: "Dictar M. O. et al, Med Mycol., 38" should be --Dictar M. O. et al, Med Mycol., 2000, 38--.

On the Title Page, Item (56), Other Publications: "Sarosi S. A." should be --Sarosi G. A.--.

In the Claims

Column 46, Line 15: "(5-nitroindolin-1yO" should be --(5-nitroindolin-1yl)--.

Signed and Sealed this
Sixteenth Day of September, 2014

Michelle K. Lee
*Deputy Director of the United States Patent and Trademark Office*